US011950863B2

(12) United States Patent
Chin et al.

(10) Patent No.: US 11,950,863 B2
(45) Date of Patent: Apr. 9, 2024

(54) SHIELDING FOR WRISTED INSTRUMENTS

(71) Applicant: Auris Health, Inc., Redwood City, CA (US)

(72) Inventors: Erica Ding Chin, Redwood City, CA (US); Travis Michael Schuh, Los Altos, CA (US)

(73) Assignee: Auris Health, Inc, Redwood City, CA (US)

( * ) Notice: Subject to any disclaimer, the term of this patent is extended or adjusted under 35 U.S.C. 154(b) by 0 days.

(21) Appl. No.: 16/711,052

(22) Filed: Dec. 11, 2019

(65) Prior Publication Data

US 2020/0197112 A1 Jun. 25, 2020

Related U.S. Application Data

(60) Provisional application No. 62/783,124, filed on Dec. 20, 2018.

(51) Int. Cl.
*A61B 34/30* (2016.01)
*A61B 17/00* (2006.01)
(Continued)

(52) U.S. Cl.
CPC .............. *A61B 34/30* (2016.02); *A61B 34/71* (2016.02); *A61B 2017/00199* (2013.01);
(Continued)

(58) Field of Classification Search
CPC ... A61B 34/30; A61B 34/71; A61B 2034/305; A61B 2034/301; A61B 2017/00199; A61B 2017/00862; A61B 2217/007; A61B 2034/2051; A61B 2090/3764; A61B 2017/00336; A61B 34/37; A61B 2217/005; A61B 2090/034; A61B 2018/146; A61B 18/1445; A61B 34/74; A61B 2017/00929; A61B 2034/105; A61B 2090/306; A61B 90/361; A61B 2034/2061;
(Continued)

(56) References Cited

U.S. PATENT DOCUMENTS 3,763,860 A 10/1973 Clarke
4,040,413 A 8/1977 Ohshiro
(Continued)

FOREIGN PATENT DOCUMENTS

CN 101443069 5/2009
CN 100515347 7/2009
(Continued)

OTHER PUBLICATIONS

International search report and written opinion dated Feb. 28, 2020 in application No. PCT/US2019/65790.

*Primary Examiner* — Erin M Piateski
*Assistant Examiner* — Ranjani Mari Sundaresan
(74) *Attorney, Agent, or Firm* — Vorys, Sater, Seymour and Pease, LLP

(57) ABSTRACT

Certain aspects relate to systems and apparatuses with shielded wrists, and methods of actuating instruments with wrists. In one aspect, an instrument includes a shaft, an end effector, and a wrist connecting the shaft to the end effector. For example, the wrist may include a proximal clevis, a distal clevis, and an intermediary frame positioned between the proximal clevis and the distal clevis.

21 Claims, 40 Drawing Sheets

(51) Int. Cl.
*A61B 34/00* (2016.01)
*A61B 34/20* (2016.01)
*A61B 34/37* (2016.01)
*A61B 90/00* (2016.01)

(52) U.S. Cl.
CPC .............. *A61B 2017/00336* (2013.01); *A61B 2017/00862* (2013.01); *A61B 2034/2051* (2016.02); *A61B 2034/301* (2016.02); *A61B 2034/305* (2016.02); *A61B 34/37* (2016.02); *A61B 2090/3764* (2016.02); *A61B 2217/005* (2013.01); *A61B 2217/007* (2013.01)

(58) Field of Classification Search
CPC .... A61B 2034/2059; A61B 2034/2065; A61B 34/20; A61G 13/10; A61G 13/04
See application file for complete search history.

(56) References Cited

U.S. PATENT DOCUMENTS

| | | | |
|---|---|---|---|
| 4,198,960 | A | 4/1980 | Utsugi |
| 4,470,407 | A | 9/1984 | Hussein |
| 4,532,935 | A | 8/1985 | Wang et al. |
| 4,685,458 | A | 8/1987 | Leckrone |
| 4,747,405 | A | 5/1988 | Leckrone |
| 4,854,301 | A | 8/1989 | Nakajima |
| 4,898,574 | A | 2/1990 | Uchiyama et al. |
| 4,983,165 | A | 1/1991 | Loiterman |
| 5,029,574 | A | 7/1991 | Shimamura et al. |
| 5,085,659 | A | 2/1992 | Rydell |
| 5,196,023 | A | 3/1993 | Martin |
| 5,217,465 | A | 6/1993 | Steppe |
| 5,308,323 | A | 5/1994 | Sogawa et al. |
| 5,318,589 | A | 6/1994 | Lichtman |
| 5,325,848 | A | 7/1994 | Adams et al. |
| 5,342,381 | A | 8/1994 | Tidemand |
| 5,344,395 | A | 9/1994 | Whalen et al. |
| 5,353,783 | A | 10/1994 | Nakao et al. |
| 5,370,609 | A | 12/1994 | Drasler et al. |
| 5,372,124 | A | 12/1994 | Takayama et al. |
| 5,411,016 | A | 5/1995 | Kume |
| 5,431,649 | A | 7/1995 | Mulier et al. |
| 5,441,485 | A | 8/1995 | Peters |
| 5,449,356 | A | 9/1995 | Walbrink |
| 5,450,843 | A | 9/1995 | Moll et al. |
| 5,472,426 | A | 12/1995 | Bonati et al. |
| 5,496,267 | A | 3/1996 | Drasler |
| 5,501,667 | A | 3/1996 | Verduin, Jr. |
| 5,520,684 | A | 5/1996 | Imran |
| 5,545,170 | A | 8/1996 | Hart |
| 5,562,239 | A | 10/1996 | Boiarski et al. |
| 5,562,648 | A | 10/1996 | Peterson |
| 5,562,678 | A | 10/1996 | Booker |
| 5,572,999 | A | 11/1996 | Funda et al. |
| 5,573,535 | A | 11/1996 | Viklund |
| 5,613,973 | A | 3/1997 | Jackson et al. |
| 5,645,083 | A | 7/1997 | Essig et al. |
| 5,653,374 | A | 8/1997 | Young et al. |
| 5,658,311 | A | 8/1997 | Baden |
| 5,695,500 | A | 12/1997 | Taylor et al. |
| 5,697,949 | A | 12/1997 | Giurtino et al. |
| 5,710,870 | A | 1/1998 | Ohm |
| 5,716,325 | A | 2/1998 | Bonutti |
| 5,788,667 | A | 8/1998 | Stoller |
| 5,792,165 | A | 8/1998 | Klieman |
| 5,797,900 | A | 8/1998 | Madhani |
| 5,810,770 | A | 9/1998 | Chin et al. |
| 5,893,869 | A | 4/1999 | Barnhart |
| 5,897,491 | A | 4/1999 | Kastenbauer et al. |
| 5,924,175 | A | 7/1999 | Lippitt |
| 5,989,230 | A | 11/1999 | Frassica |
| 6,071,281 | A | 6/2000 | Burnside et al. |
| 6,093,157 | A | 7/2000 | Chandrasekaran |
| 6,110,171 | A | 8/2000 | Rydell |
| 6,120,476 | A | 9/2000 | Fung et al. |
| 6,120,498 | A | 9/2000 | Jani et al. |
| 6,156,030 | A | 12/2000 | Neev |
| 6,174,318 | B1 | 1/2001 | Bates et al. |
| 6,206,903 | B1 | 3/2001 | Ramans |
| 6,183,435 | B1 | 6/2001 | Bumbalough et al. |
| 6,322,557 | B1 | 11/2001 | Nikolaevich |
| 6,375,635 | B1 | 4/2002 | Moutafis |
| 6,394,998 | B1 | 5/2002 | Wallace et al. |
| 6,405,078 | B1 | 6/2002 | Moaddeb et al. |
| 6,440,061 | B1 | 8/2002 | Wenner et al. |
| 6,508,823 | B1 | 1/2003 | Gonon |
| 6,522,906 | B1 | 2/2003 | Salisbury et al. |
| 6,577,891 | B1 | 6/2003 | Jaross et al. |
| 6,676,668 | B2 | 1/2004 | Mercereau et al. |
| 6,685,698 | B2 | 2/2004 | Morley et al. |
| 6,706,050 | B1 | 3/2004 | Giannadakis |
| 7,282,055 | B2 | 10/2007 | Tsuruta |
| 7,559,934 | B2 | 7/2009 | Teague et al. |
| 7,736,356 | B2 | 6/2010 | Cooper et al. |
| 7,963,911 | B2 | 6/2011 | Turliuc |
| 7,987,046 | B1 | 7/2011 | Peterman |
| 8,002,713 | B2 | 8/2011 | Heske |
| 8,038,598 | B2 | 10/2011 | Khachi |
| 8,092,397 | B2 | 1/2012 | Wallace et al. |
| 8,187,173 | B2 | 5/2012 | Miyoshi |
| 8,257,303 | B2 | 9/2012 | Moll et al. |
| 8,480,595 | B2 | 7/2013 | Speeg |
| 8,523,762 | B2 | 9/2013 | Miyamoto et al. |
| 8,540,748 | B2 | 9/2013 | Murphy et al. |
| 8,820,603 | B2 | 9/2014 | Shelton et al. |
| 8,882,660 | B2 * | 11/2014 | Phee ..................... A61B 34/37 600/139 |
| 8,945,163 | B2 | 2/2015 | Voegele et al. |
| 8,956,280 | B2 | 2/2015 | Eversull et al. |
| 9,345,456 | B2 | 5/2016 | Tsonton et al. |
| 9,460,536 | B2 | 10/2016 | Hasegawa et al. |
| 9,504,604 | B2 | 11/2016 | Alvarez |
| 9,561,083 | B2 | 2/2017 | Yu et al. |
| 9,592,042 | B2 | 3/2017 | Titus |
| 9,597,152 | B2 | 3/2017 | Schaeffer |
| 9,622,827 | B2 | 4/2017 | Yu et al. |
| 9,636,184 | B2 | 5/2017 | Lee et al. |
| 9,713,509 | B2 | 7/2017 | Schuh et al. |
| 9,727,963 | B2 | 8/2017 | Mintz et al. |
| 9,730,757 | B2 | 8/2017 | Brudniok |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,080,576 | B2 | 9/2018 | Romo et al. |
| 10,136,959 | B2 | 11/2018 | Mintz et al. |
| 10,145,747 | B1 | 12/2018 | Lin et al. |
| 10,149,720 | B2 | 12/2018 | Romo |
| 10,159,532 | B1 | 12/2018 | Ummalaneni et al. |
| 10,159,533 | B2 | 12/2018 | Moll et al. |
| 10,169,875 | B2 | 1/2019 | Mintz et al. |
| 10,219,874 | B2 | 3/2019 | Yu et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,285,574 | B2 | 5/2019 | Landey et al. |
| 10,299,870 | B2 | 5/2019 | Connolly et al. |
| 10,314,463 | B2 | 6/2019 | Agrawal et al. |
| 10,350,390 | B2 | 7/2019 | Moll et al. |
| 10,383,765 | B2 | 8/2019 | Alvarez et al. |
| 10,398,518 | B2 | 9/2019 | Yu et al. |

(56) References Cited

U.S. PATENT DOCUMENTS

| | | |
|---|---|---|
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 2002/0019644 A1 | 2/2002 | Hastings |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0119870 A1* | 5/2008 | Williams ............... A61B 34/37 606/130 |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1* | 12/2009 | Cabrera ............. A61B 17/0469 606/144 |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1* | 1/2010 | Manzo ............... A61B 18/1445 606/46 |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0138660 A1 | 6/2012 | Shelton, IV et al. |
| 2012/0209315 A1 | 8/2012 | Amat |
| 2012/0232338 A1* | 9/2012 | Livneh ............... A61B 1/00101 600/104 |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0123805 A1 | 5/2013 | Park et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0233908 A1 | 9/2013 | Knodel |
| 2013/0253267 A1 | 9/2013 | Collins |

(56) References Cited

U.S. PATENT DOCUMENTS

| | | |
|---|---|---|
| 2013/0303876 A1 | 11/2013 | Gelfand et al. |
| 2013/0310819 A1 | 11/2013 | Neuberger et al. |
| 2013/0334281 A1 | 12/2013 | Williams |
| 2013/0345686 A1 | 12/2013 | Brown |
| 2014/0005681 A1 | 1/2014 | Gee et al. |
| 2014/0005705 A1* | 1/2014 | Weir ............... A61B 34/37 606/169 |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam et al. |
| 2014/0246473 A1 | 9/2014 | Auld |
| 2014/0275956 A1 | 9/2014 | Fan |
| 2014/0276723 A1 | 9/2014 | Parihar |
| 2014/0276956 A1 | 9/2014 | Crainich |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2015/0080879 A1 | 3/2015 | Trees |
| 2015/0127045 A1 | 5/2015 | Prestel |
| 2015/0133960 A1 | 5/2015 | Lohmeier |
| 2015/0164522 A1 | 6/2015 | Budiman |
| 2015/0201917 A1 | 7/2015 | Snow |
| 2015/0202085 A1 | 7/2015 | Lemonis |
| 2015/0314110 A1 | 11/2015 | Park |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Isakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2017/0007255 A1* | 1/2017 | Jaworek ............ A61B 18/1442 |
| 2017/0007337 A1 | 1/2017 | Dan |
| 2017/0049471 A1 | 2/2017 | Gaffney et al. |
| 2017/0055995 A1 | 3/2017 | Weier |
| 2017/0056068 A1* | 3/2017 | Hess ............... A61B 17/29 |
| 2017/0065227 A1 | 3/2017 | Marrs |
| 2017/0095234 A1 | 4/2017 | Prisco et al. |
| 2017/0095295 A1 | 4/2017 | Overmyer |
| 2017/0135706 A1 | 5/2017 | Frey |
| 2017/0151416 A1 | 6/2017 | Kutikov |
| 2017/0172553 A1 | 6/2017 | Chaplin |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0265923 A1 | 9/2017 | Privitera |
| 2017/0265954 A1 | 9/2017 | Burbank |
| 2017/0290631 A1 | 10/2017 | Lee et al. |
| 2017/0319289 A1 | 11/2017 | Neff et al. |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0099231 A1 | 4/2019 | Bruehwiler |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0163726 A1 | 5/2020 | Tanner |
| 2020/0188043 A1 | 6/2020 | Yu |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |

FOREIGN PATENT DOCUMENTS

| | | |
|---|---|---|
| CN | 103298414 | 9/2013 |
| CN | 205729413 | 11/2016 |
| EP | 1 321 106 | 6/2003 |
| EP | 1 849 423 | 10/2007 |
| EP | 2676615 A2 | 12/2013 |
| JP | 2005-270464 | 10/2005 |
| WO | WO-2011078971 A1 | 6/2011 |
| WO | WO 11/161218 | 12/2011 |
| WO | WO 13/107468 | 7/2013 |
| WO | WO-2015027250 A1 | 3/2015 |
| WO | WO-2015127250 A1 | 8/2015 |
| WO | WO 17/114855 | 7/2017 |

(56) References Cited

FOREIGN PATENT DOCUMENTS

| WO | WO-2017136710 A2 * | 8/2017 | ............ A61B 17/29 |
| WO | WO 18/069679 | 4/2018 | |
| WO | WO 18/189722 | 10/2018 | |

* cited by examiner

SHIELDING FOR WRISTED INSTRUMENTS

CROSS-REFERENCE TO RELATED APPLICATION(S)

This application claims the benefit of U.S. Provisional Application No. 62/783,124, filed Dec. 20, 2018, which is hereby incorporated by reference in its entirety.

TECHNICAL FIELD

The systems and methods disclosed herein are directed to systems with shielding for instrument wrists, and more particularly to wristed medical instruments including a sheath.

BACKGROUND

Certain wristed instruments use sheathing, which at least partially covers the wrist, for electrical insulation or sealing purposes. For example, certain monopolar instruments, such as monopolar scissors, may use sheathing to prevent tissue from being inadvertently burned due to stray electrical current being applied to tissue from locations other than an end effector of the scissors. The sheath can serve as a cover or sleeve that can be placed over the instrument before use in a surgery, or may be permanently fixed over the instrument wrist. The sheathing can extend from the instrument shaft to the end effector and can be designed to cover the wrist throughout a medical procedure.

SUMMARY

The systems, methods and devices of this disclosure each have several innovative aspects, no single one of which is solely responsible for the desirable attributes disclosed herein.

In one aspect, there is provided an instrument, comprising: a shaft; an end effector; and a wrist connecting the shaft to the end effector, the wrist comprising a proximal clevis, a distal clevis, and an intermediary frame positioned between the proximal clevis and the distal clevis.

In another aspect, there is provided an instrument, comprising: a shaft; a wrist comprising a proximal clevis and distal clevis that form a rolling joint; and a mechanical stop configured to limit a pitch angle between the proximal clevis and the distal clevis.

In yet another aspect, there is provided a method of actuating an instrument, the instrument comprising an end effector and a wrist, the method comprising: advancing or retracting at least one cable segment that engages a distal clevis of the instrument, the wrist comprising a proximal clevis, the distal clevis, and an intermediary frame positioned between the proximal clevis and the distal clevis, wherein the advancing or retracting at least one cable segment articulates the distal clevis with respect to the proximal clevis.

In still yet another aspect, there is provided an instrument, comprising: a shaft; an end effector; a mechanical hardstop; and a wrist connecting the shaft to the end effector, the wrist comprising a proximal clevis and a distal clevis, wherein the hardstop is configured to serve as a mechanical stop to limit a pitch angle between the proximal clevis and the distal clevis.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
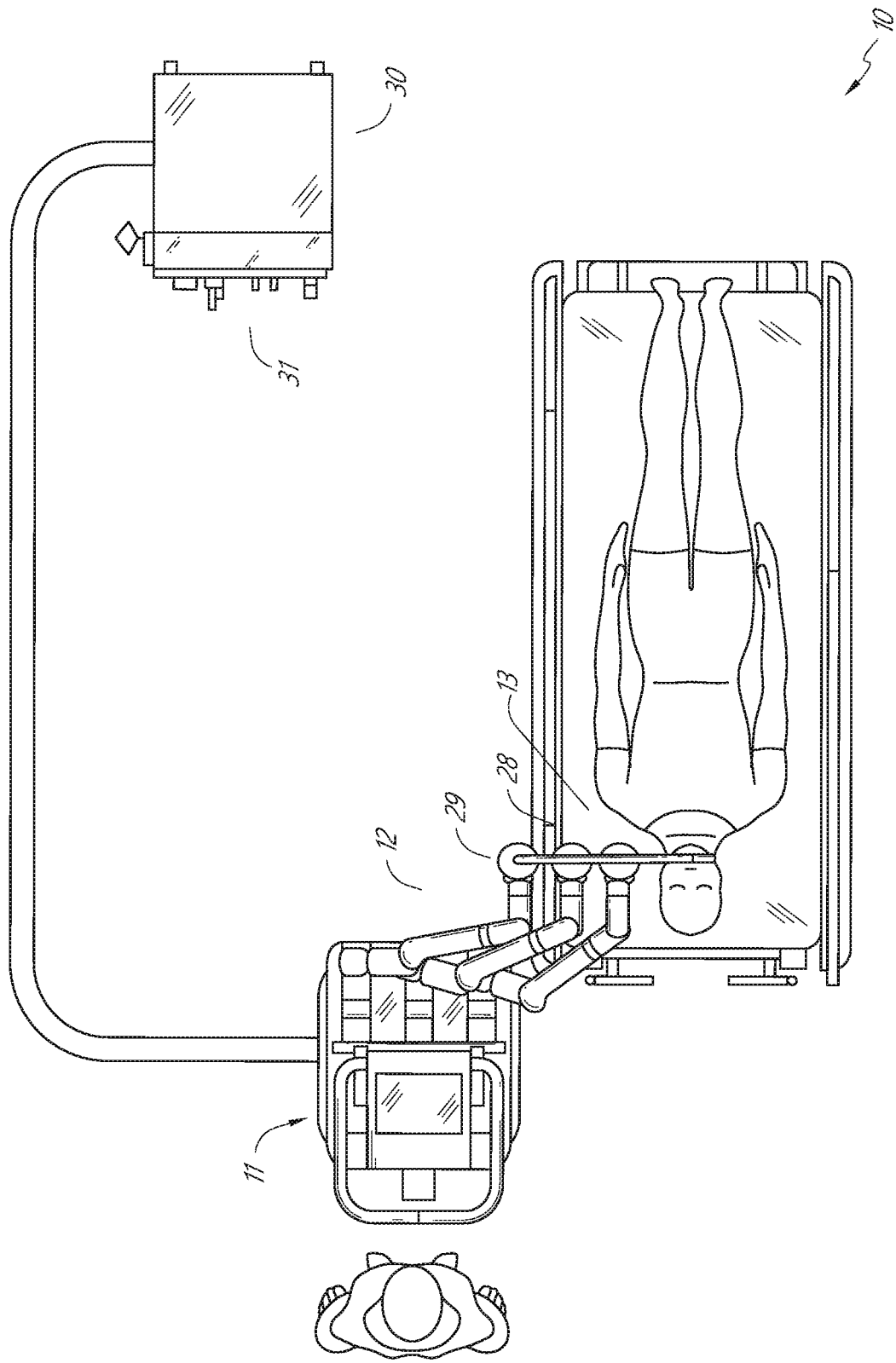
FIG. 1 illustrates an embodiment of a cart-based robotic system arranged for diagnostic and/or therapeutic bronchoscopy.
Figure 2:
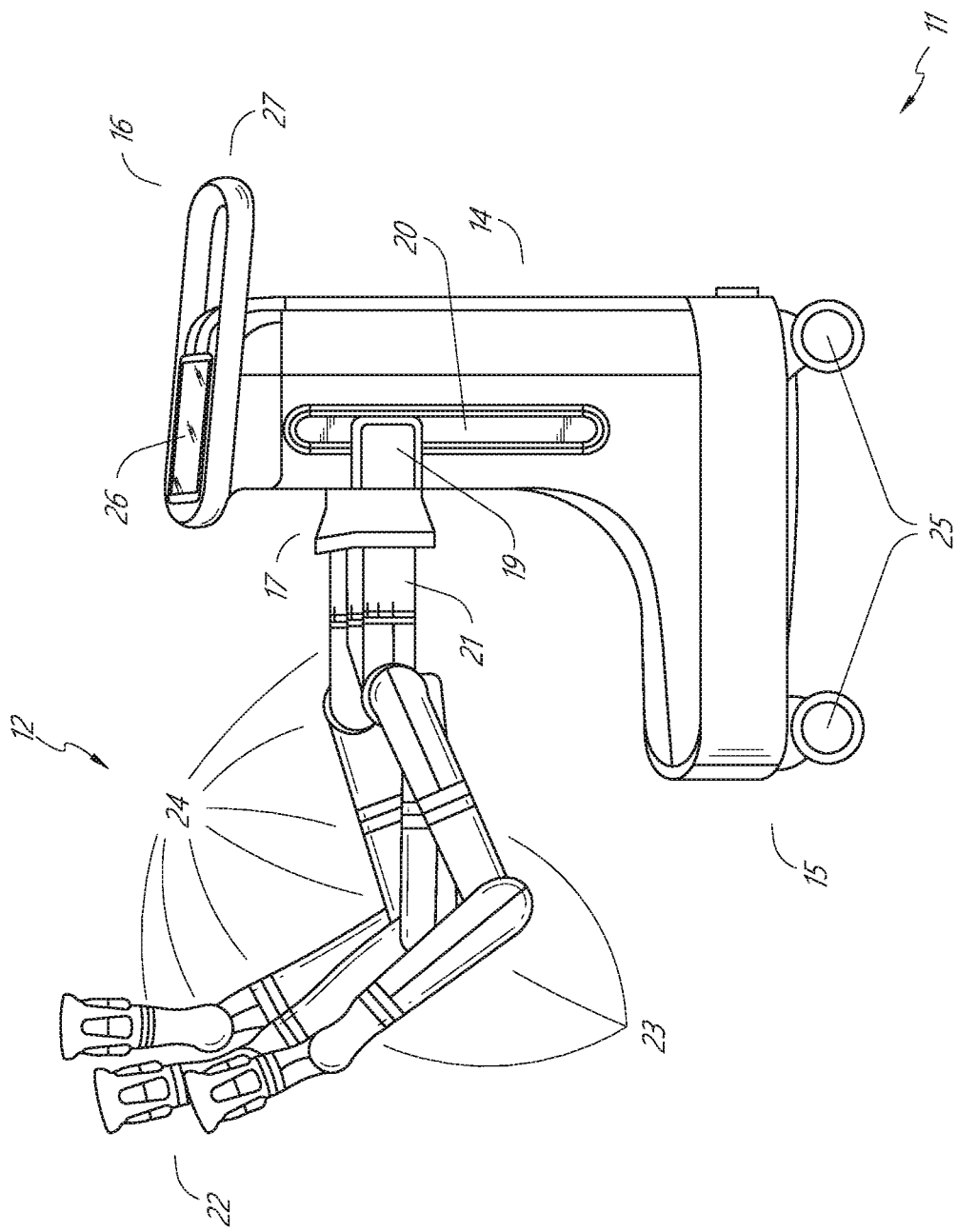
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles.

This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
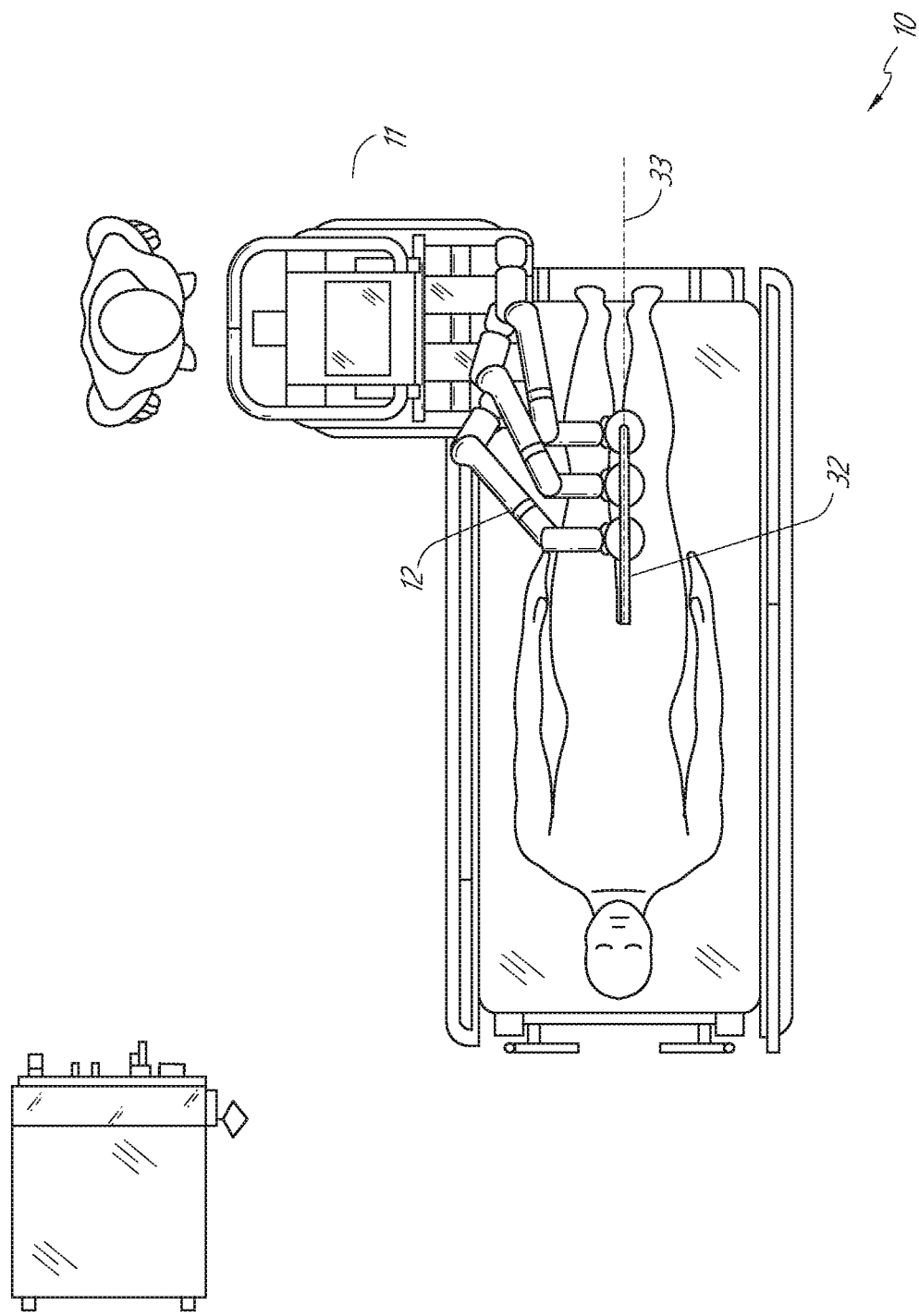
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
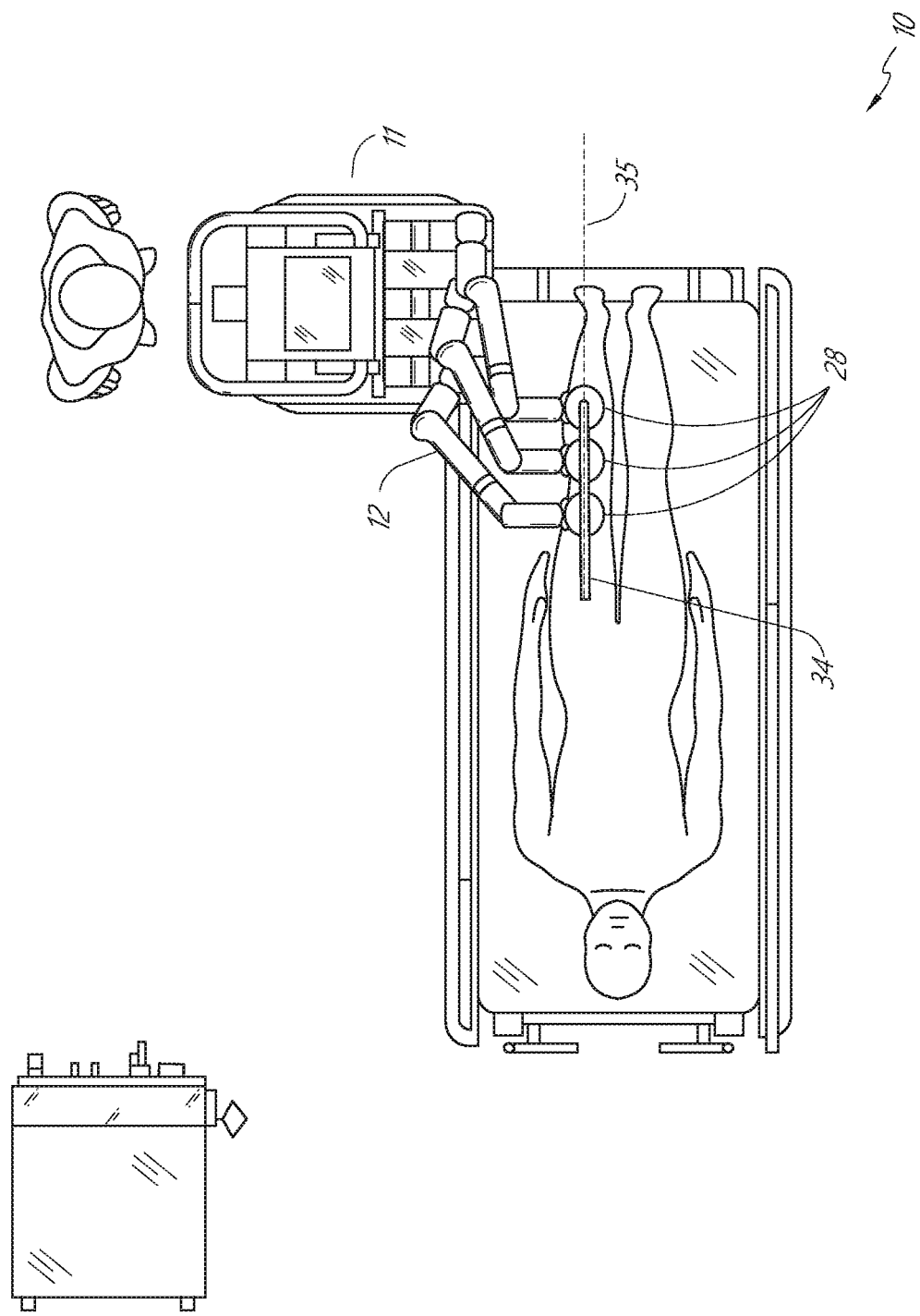
FIG. 4 illustrates an embodiment of the robotic system of FIG. 1 arranged for a vascular procedure.

FIG. 4 illustrates an embodiment of a robotically-enabled 10 system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
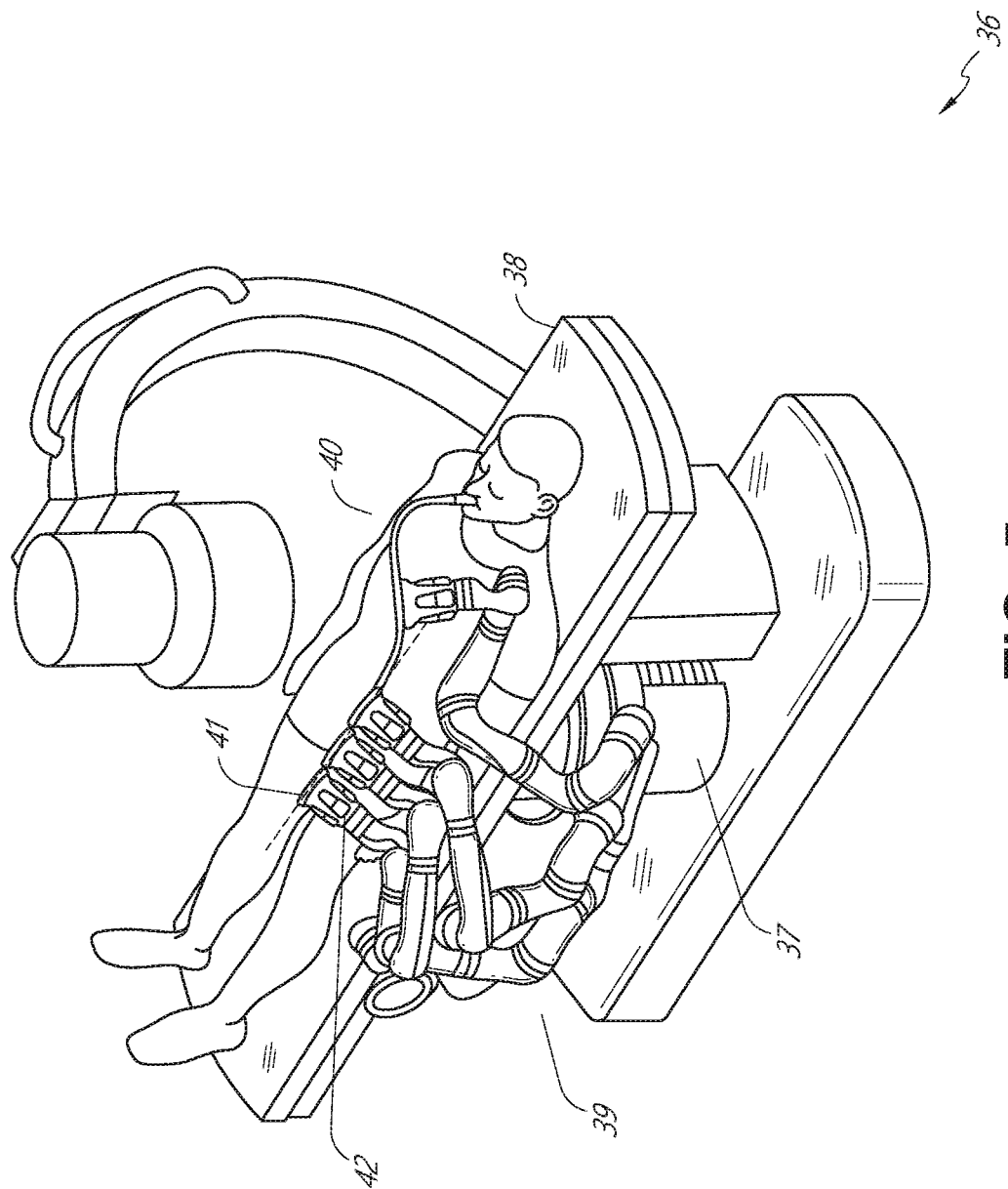
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
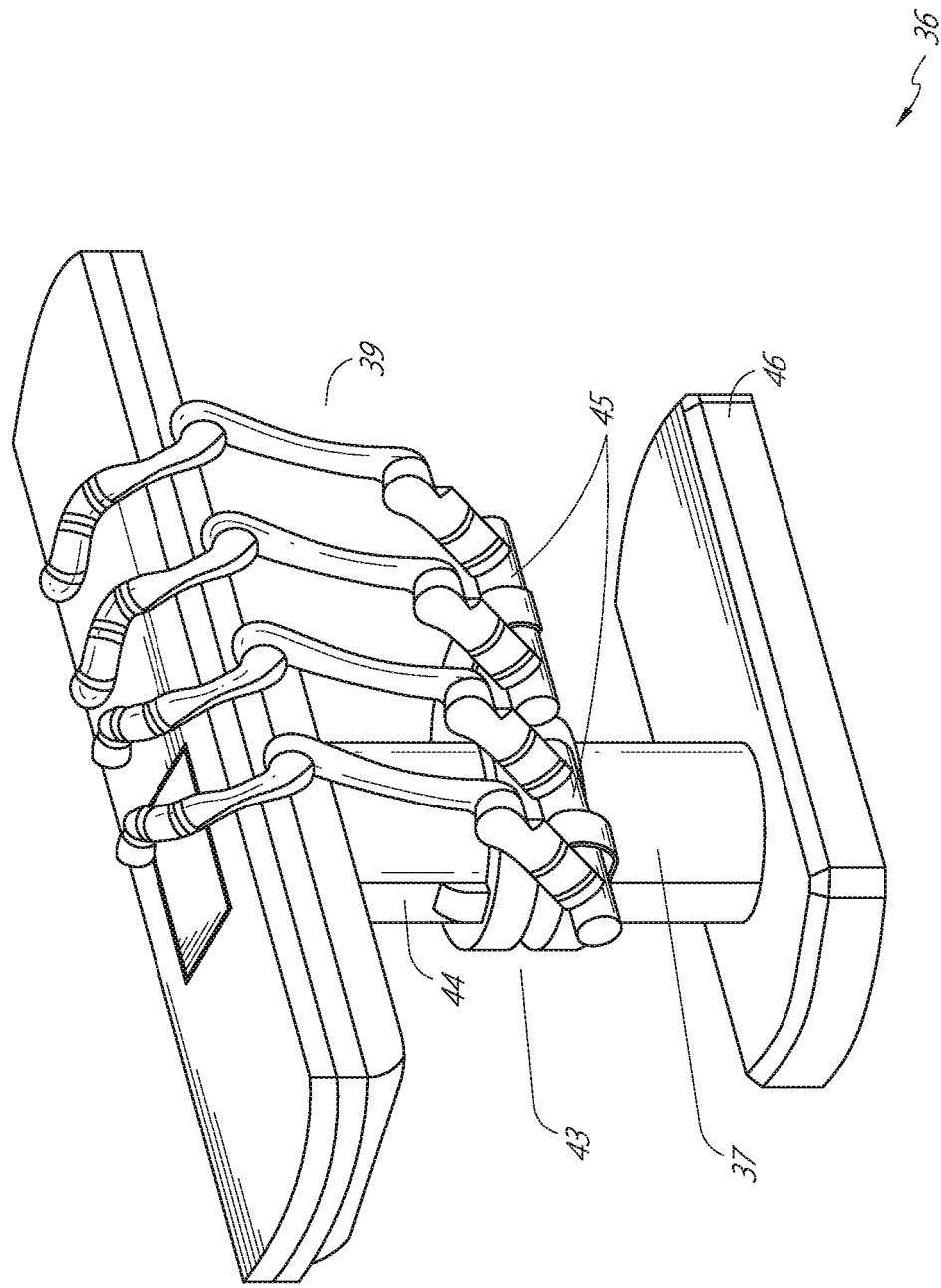
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
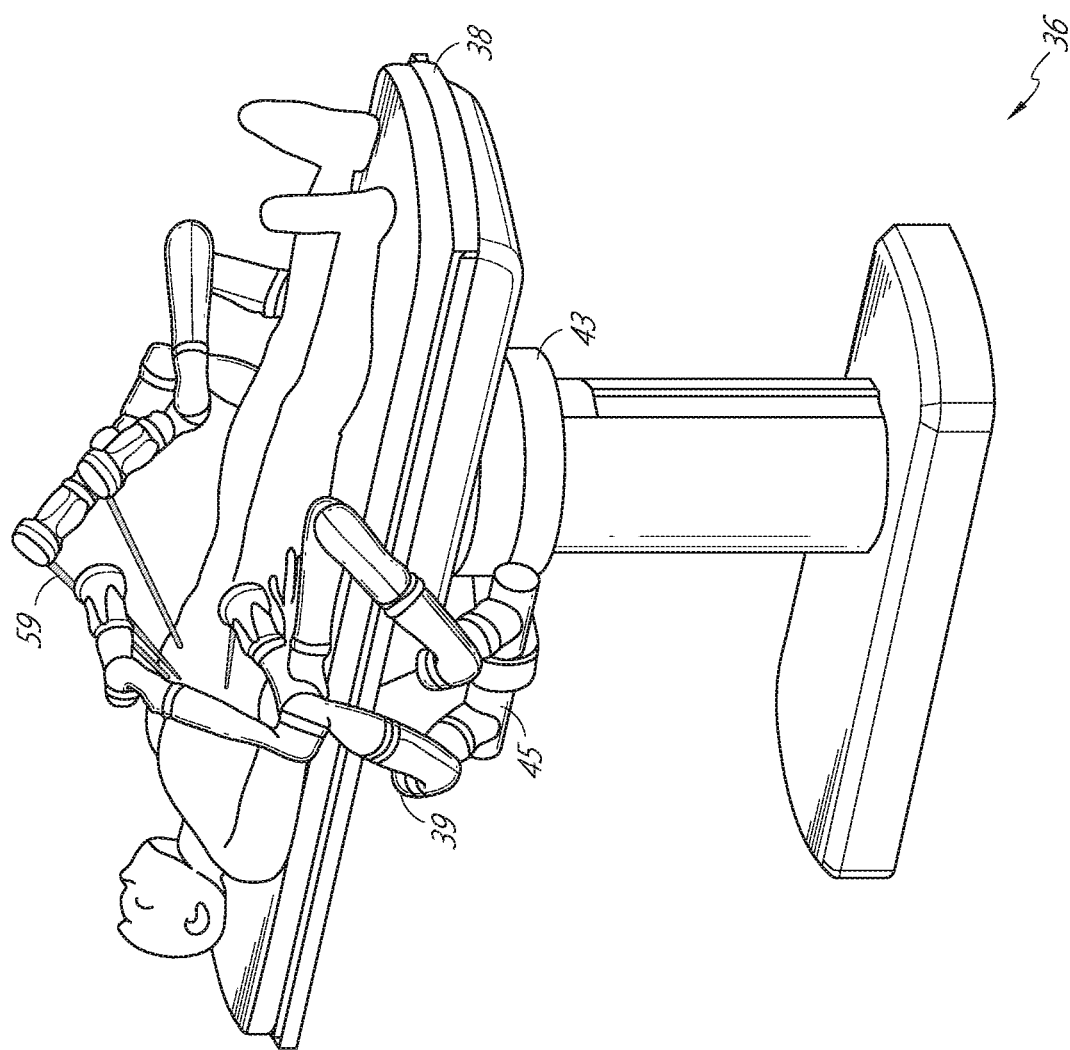
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
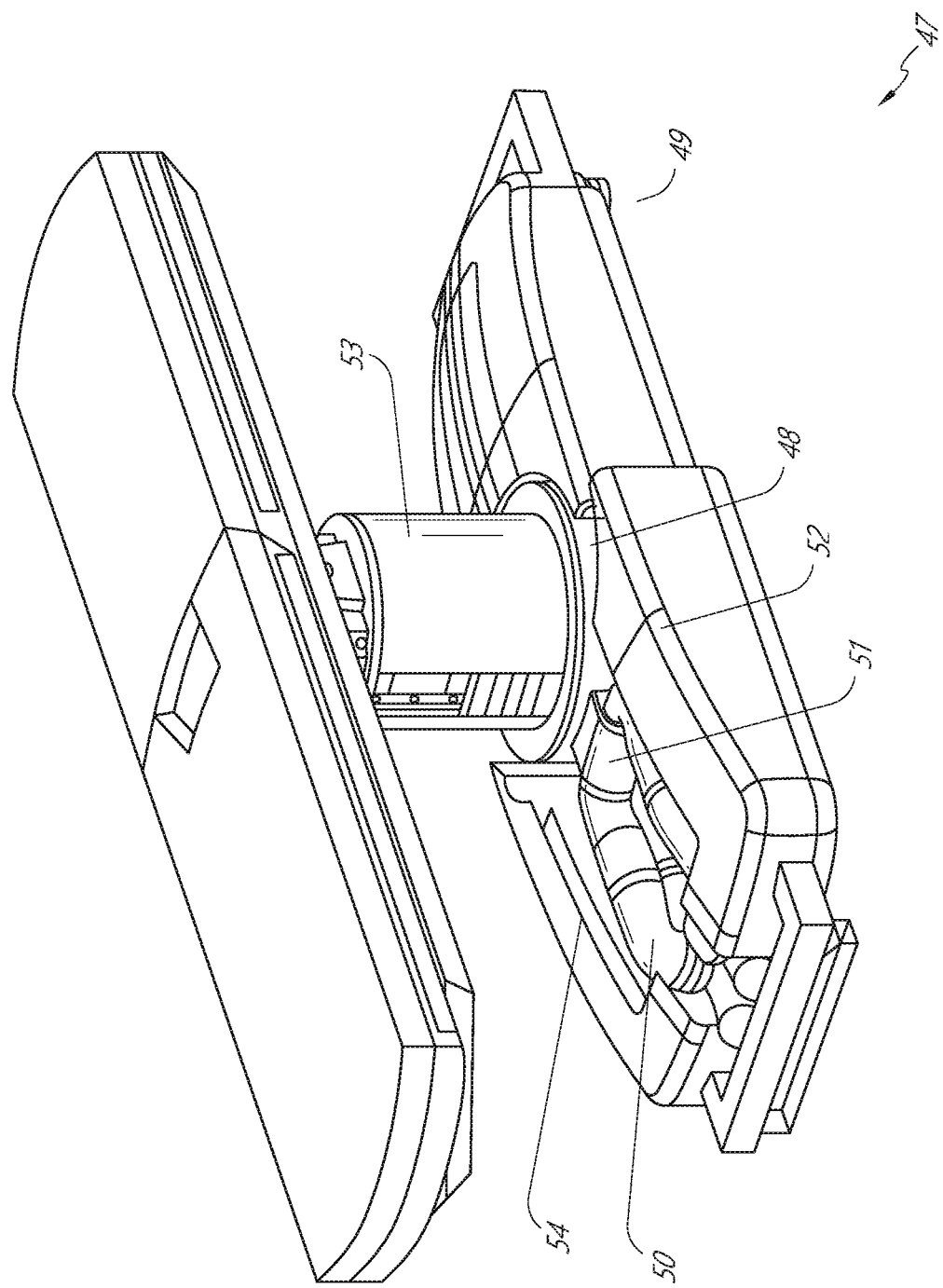
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
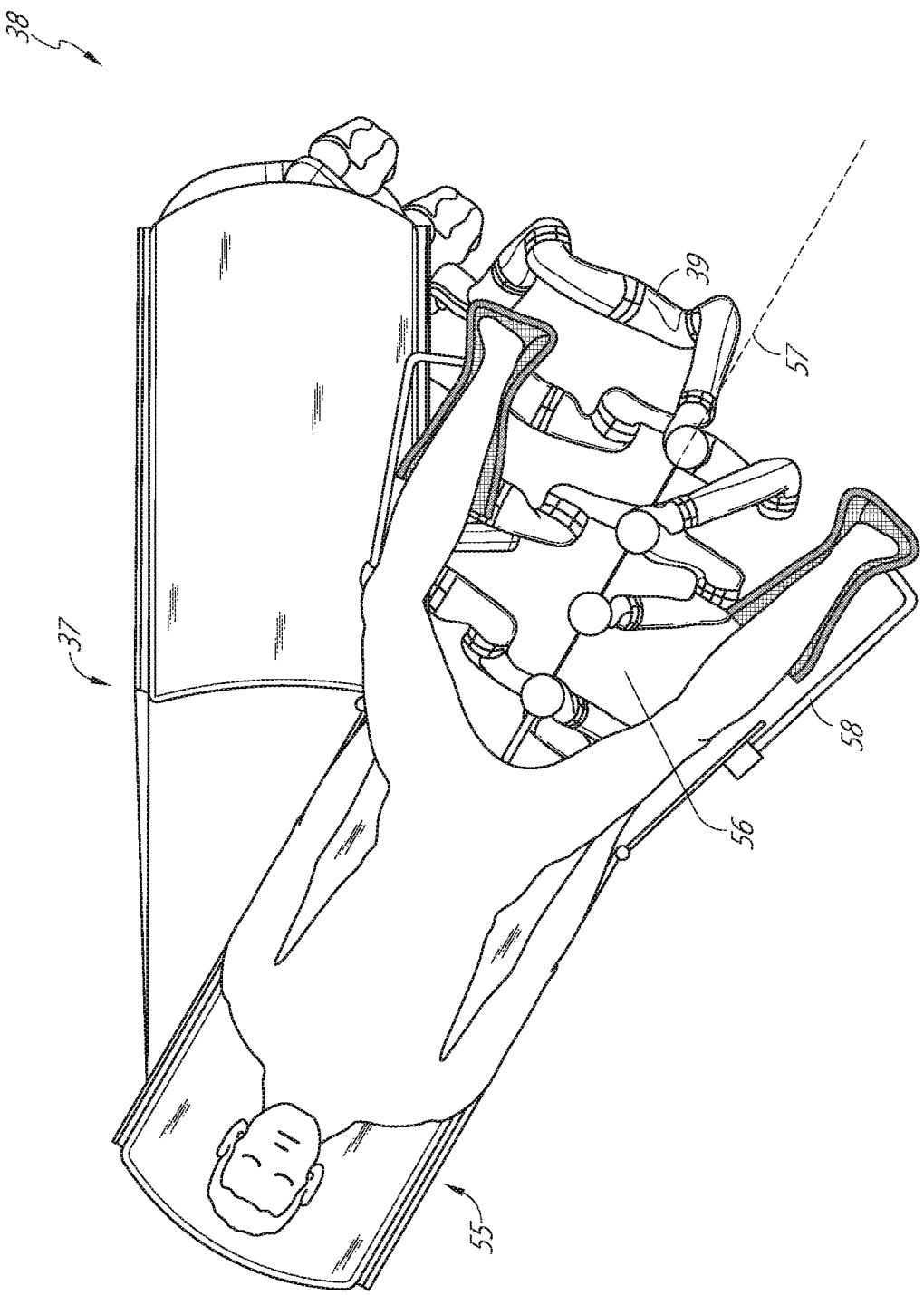
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
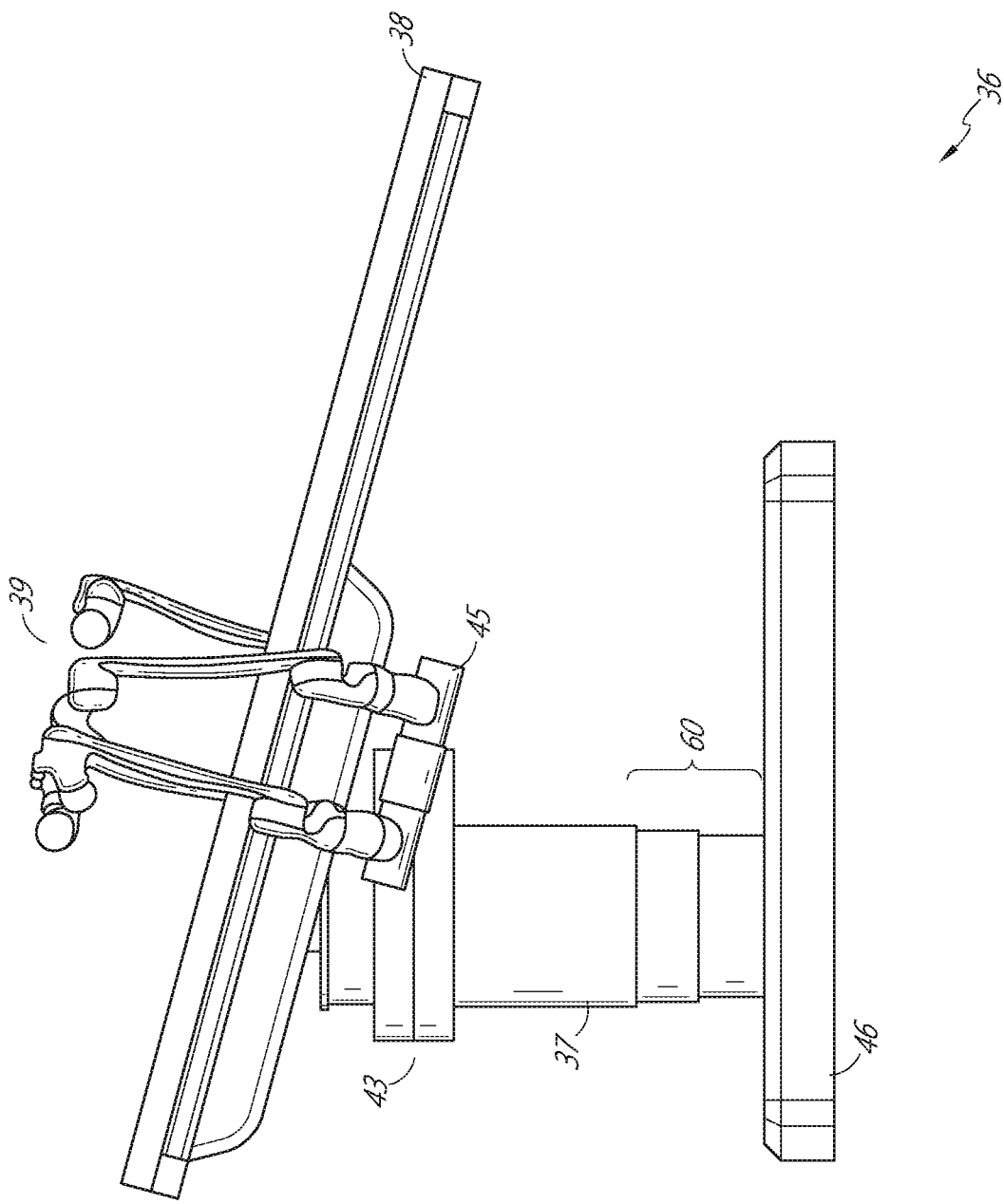
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
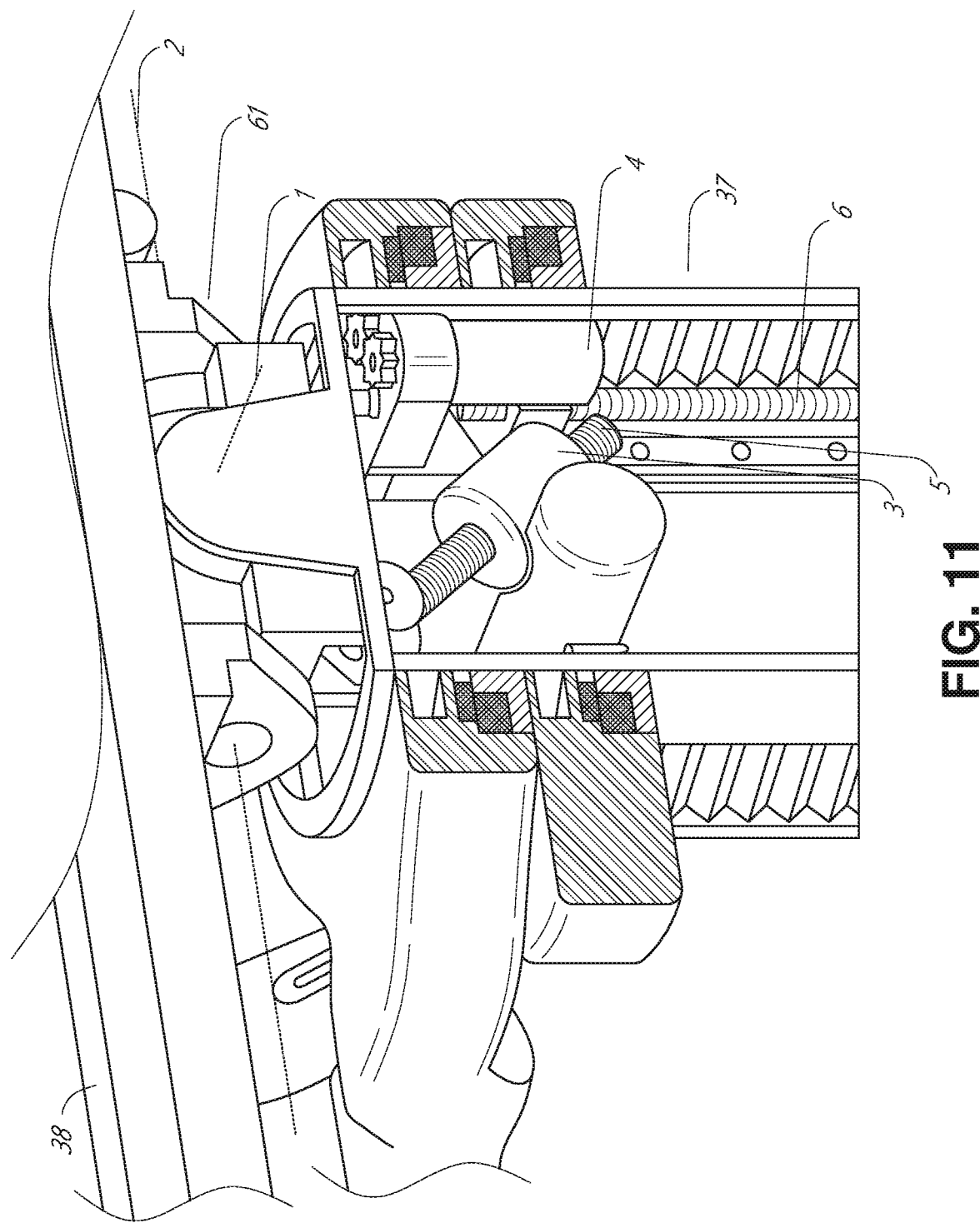
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
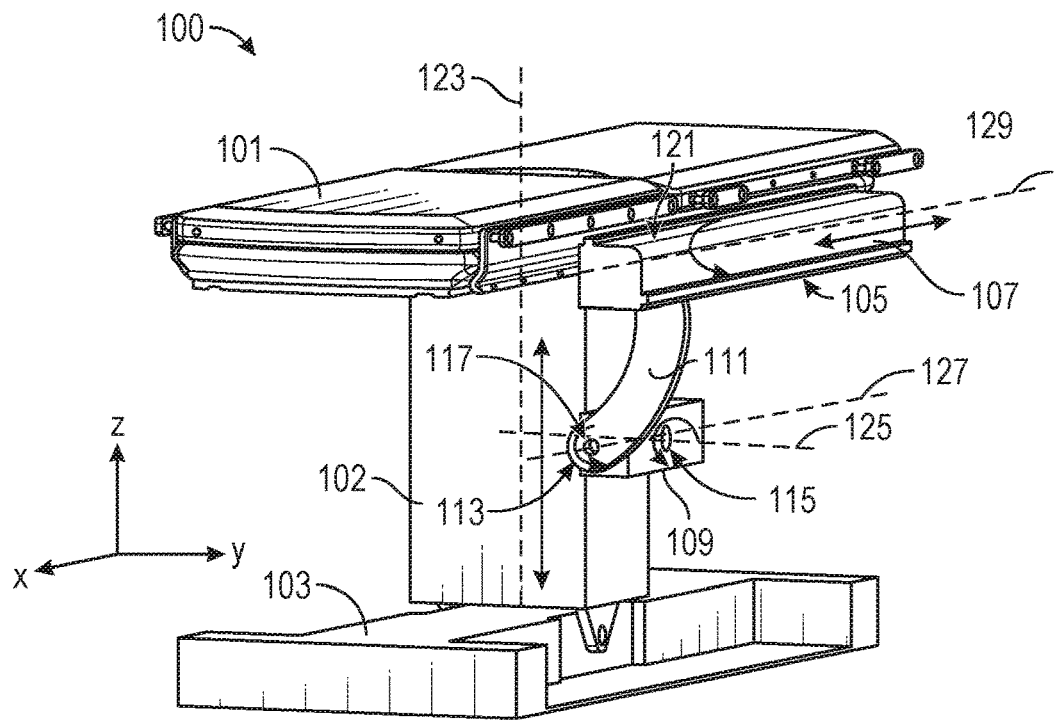
FIG. 12 illustrates an alternative embodiment of a table-based robotic system.
Figure 13:
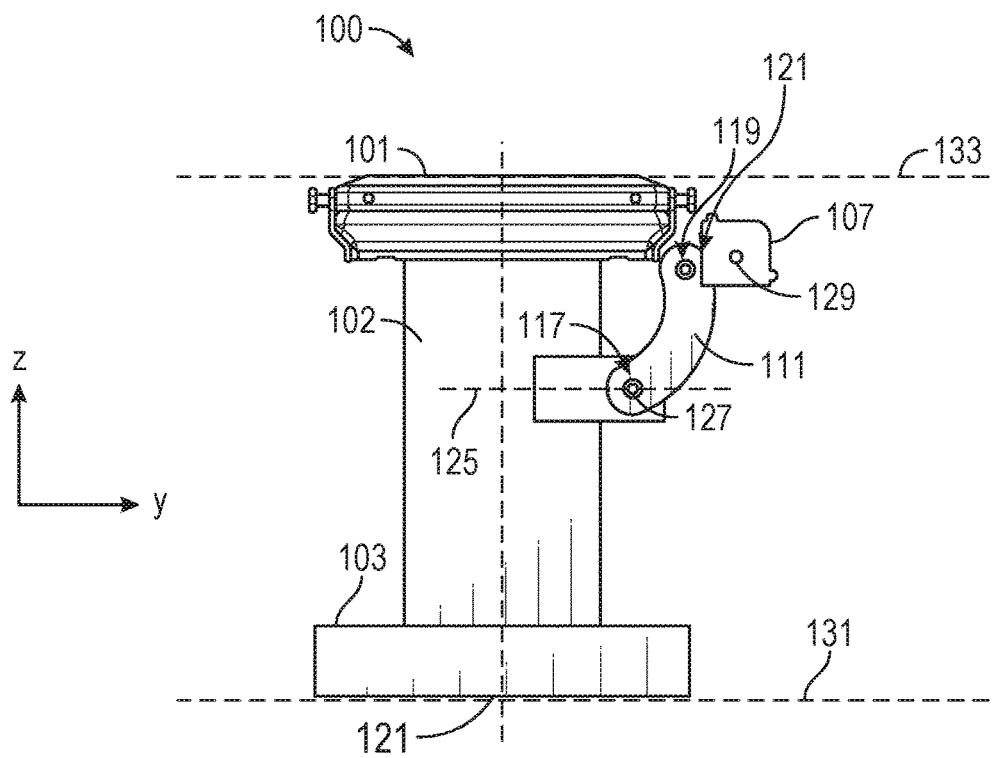
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
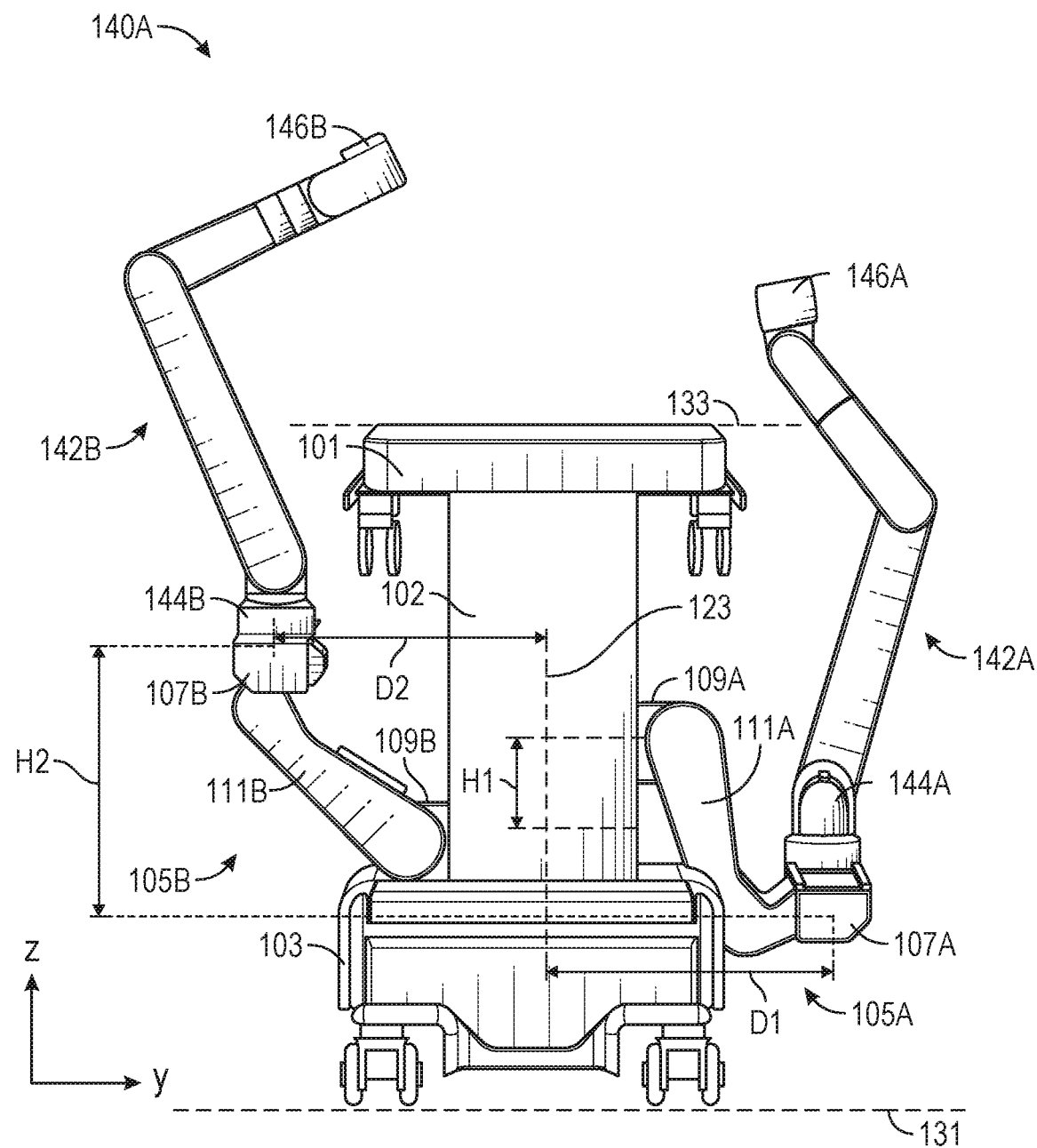
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
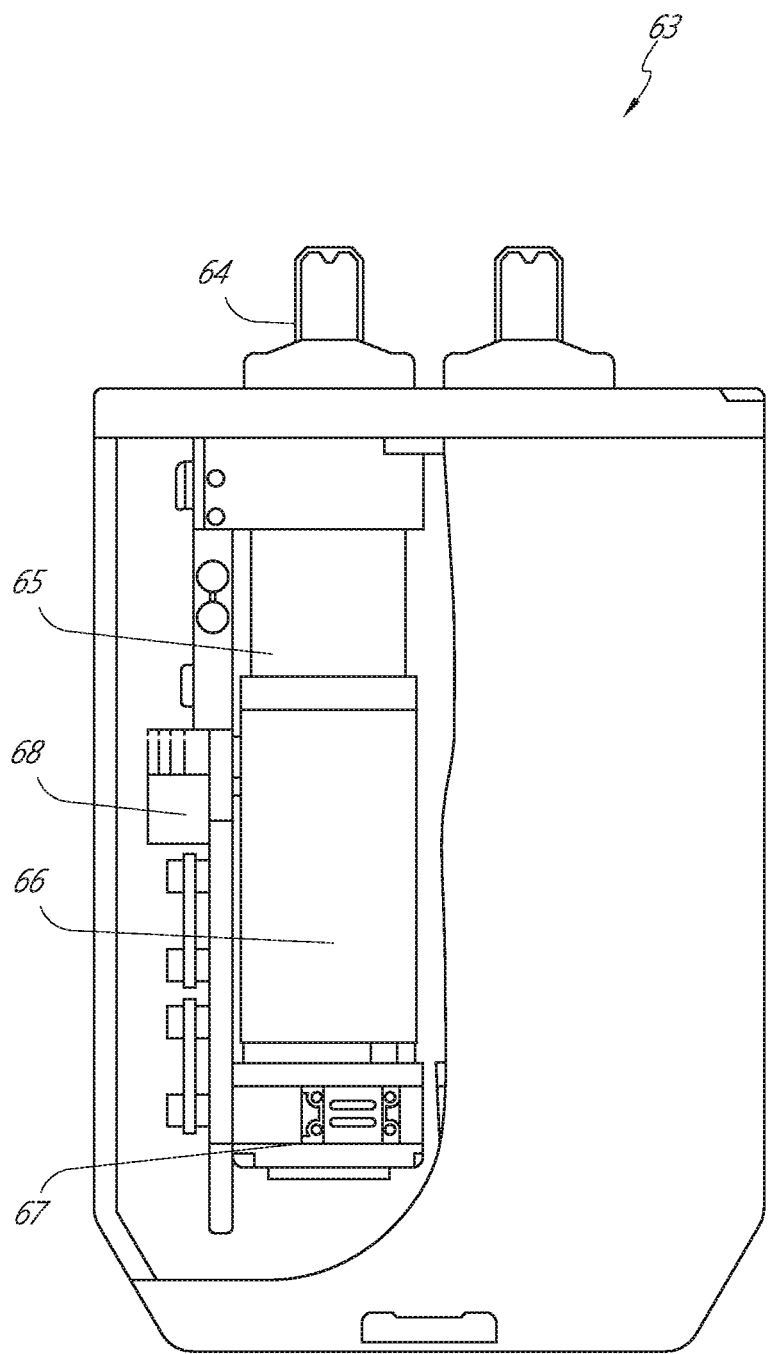
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
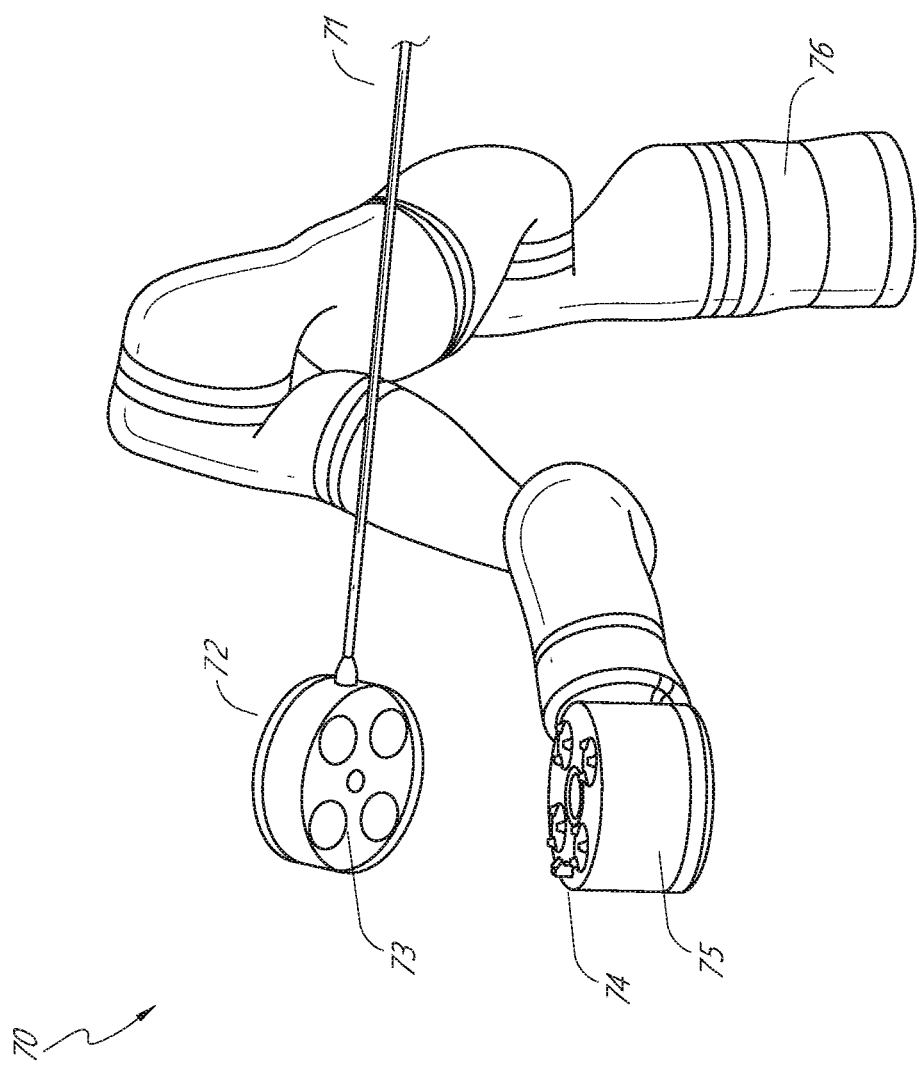
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
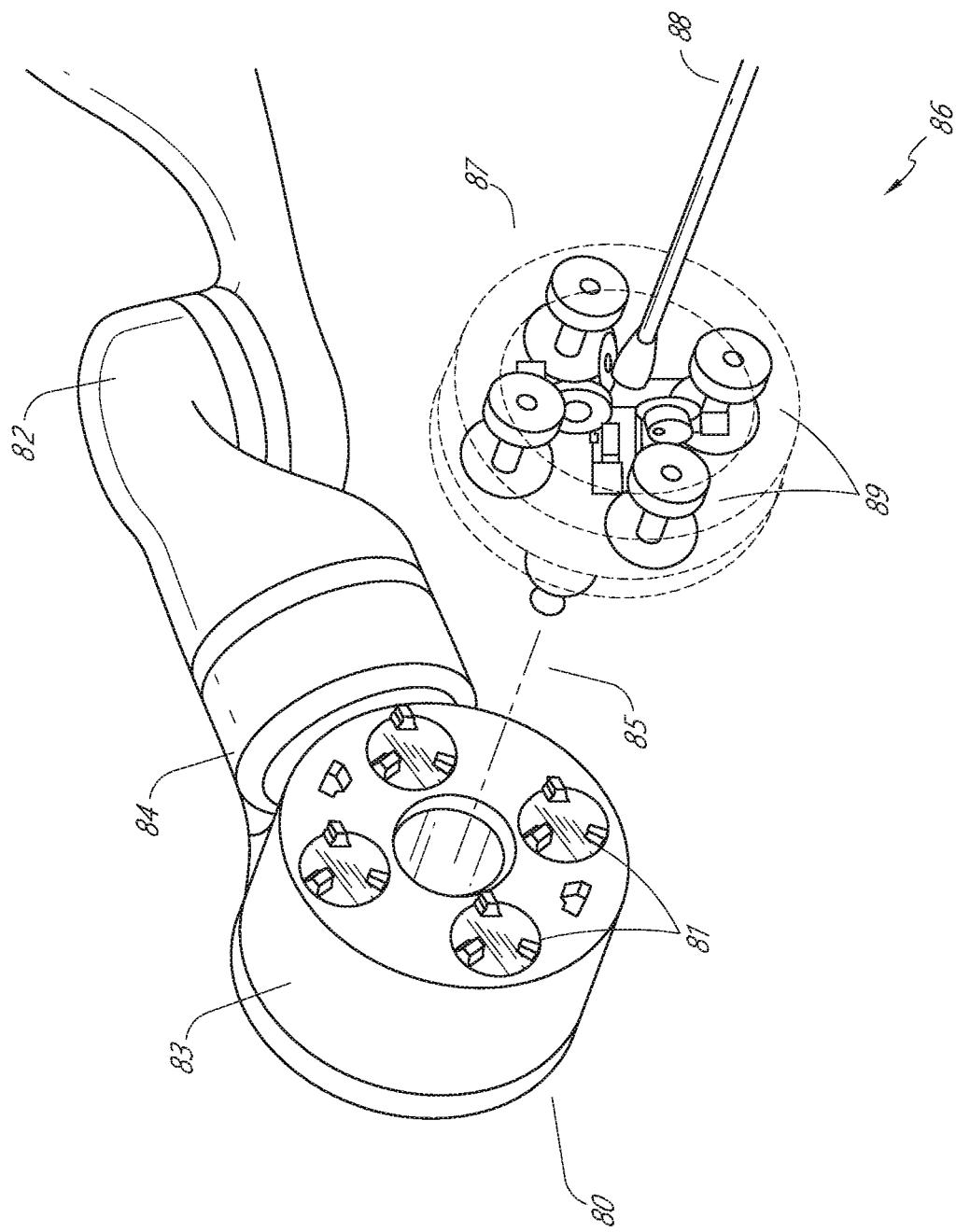
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
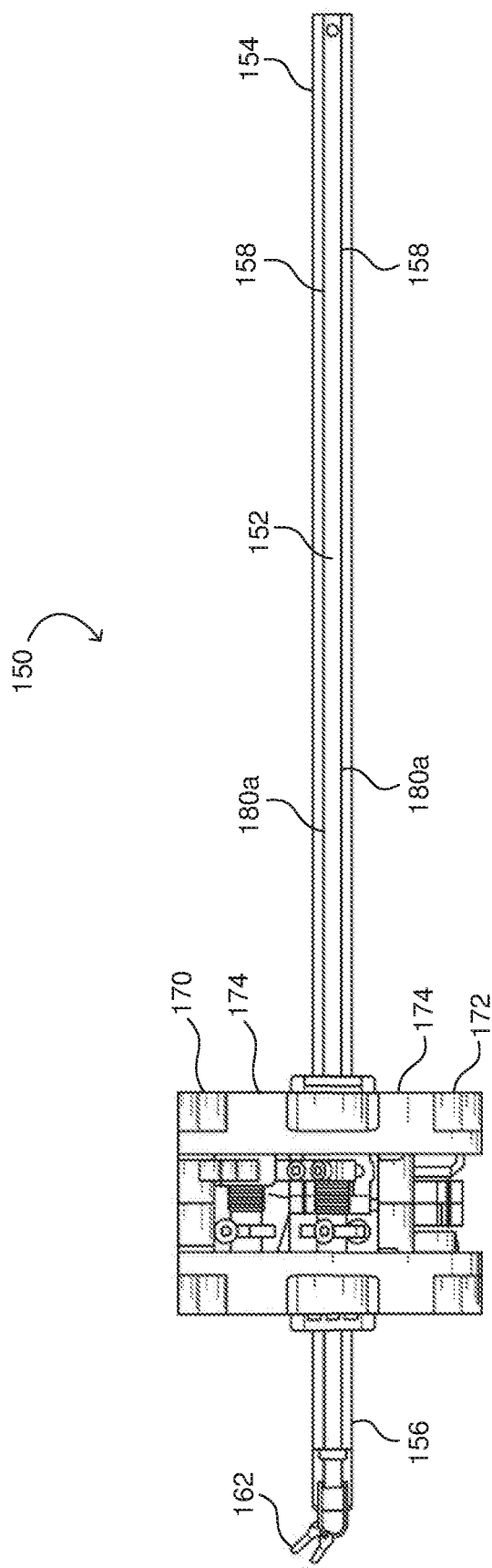
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
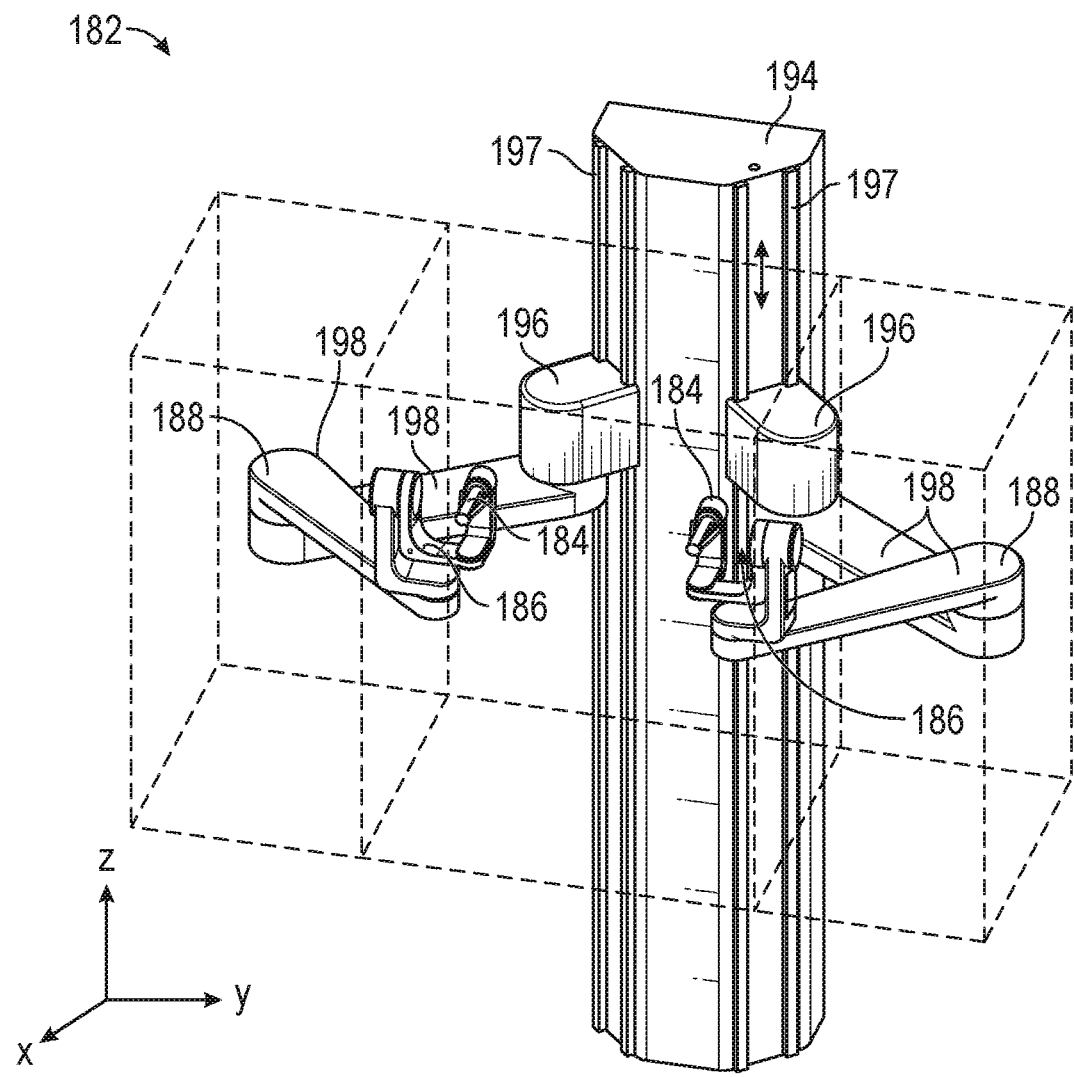
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
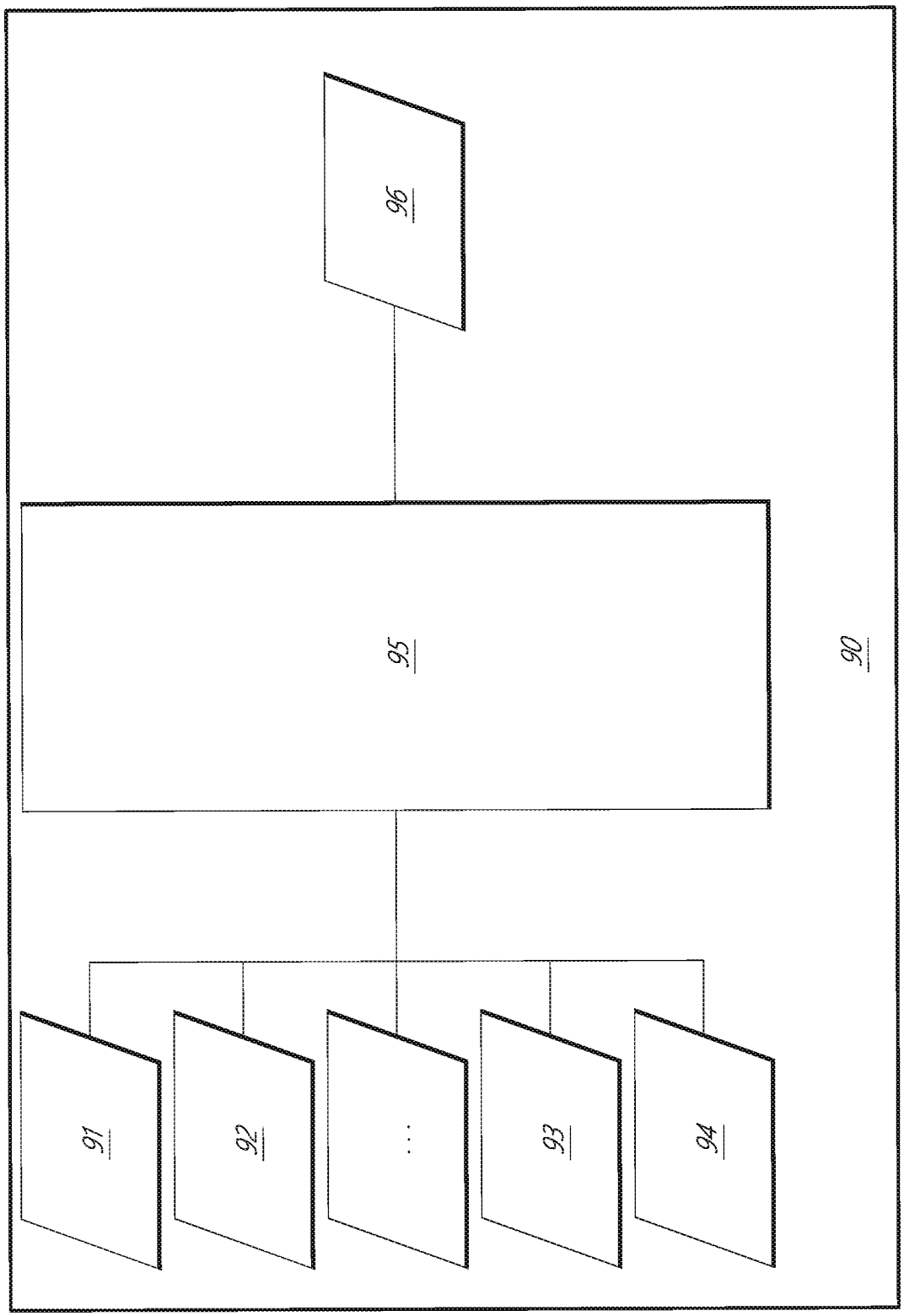
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Shielded Wrists for Instruments

Figure 21:
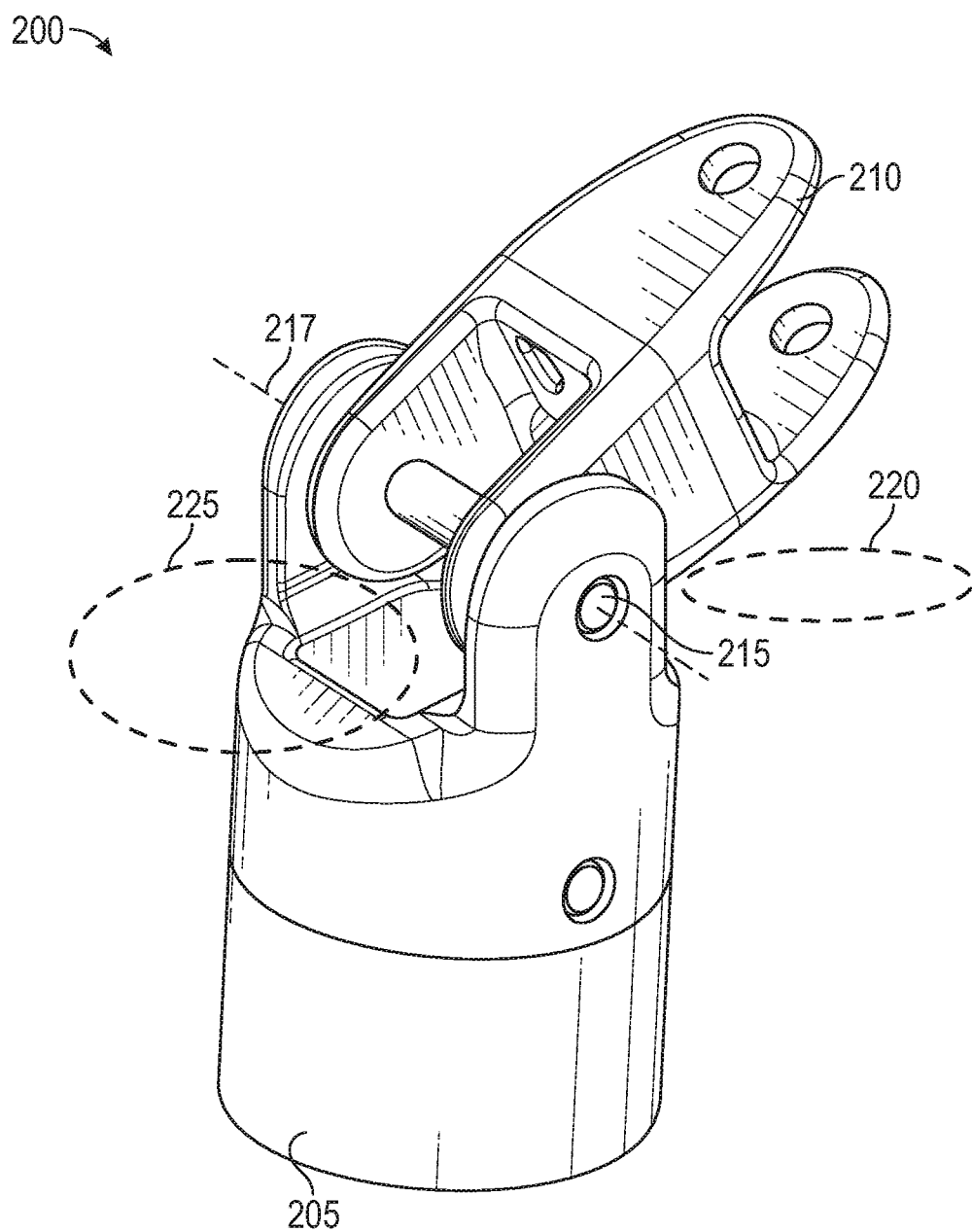
FIG. 21 illustrates one embodiment of an instrument wrist in accordance with aspects of this disclosure.

Embodiments of the disclosure relate to improved shielding for wristed instruments. FIG. 21 illustrates one embodiment of an instrument wrist in accordance with aspects of this disclosure. As shown in FIG. 21, the instrument 200 includes: a proximal clevis 205; a distal clevis 210; and a pin joint 215 forming a pitch axis 217. The distal clevis 210 is configured to be articulated with respect to the proximal clevis 205 around the pitch axis 217. As used herein, the point of articulation between the proximal and distal clevises 205 and 210 may be referred to as a "wrist." Depending on the embodiment, the wrist may include additional degrees of freedom of movement (e.g., additional axes around which at least a portion of the instrument 200 can be articulated).

The instrument 200 may benefit from the inclusion of a sheath (not illustrated in FIG. 21) formed over at least a portion of the wrist. The sheath may shield at least a portion of the wrist of the instrument 200 from the environment. The sheath may be formed of a flexible material, an elastomeric material, an electrically insulating material, etc. In some embodiments, the instrument 200 can also include an end effector, such as a monopolar scissors, which may apply a current through tissue to a grounding pad. In this embodiment, the sheath may electrically insulate the wrist from the patient, thereby preventing current from flowing to/from the patient via the wrist. The sheath may also substantially seal the wrist such that fluids or other foreign materials can be prevented from penetrating into the moving parts of the wrist.

The sheath may be formed of a flexible material in order to enable freedom of movement of the wrist. As the distal clevis 210 is articulated, the sheath can be inadvertently pinched and torn by the wrist. In particular, as shown in FIG. 21, in the regions 220 and 225 illustrated by circles, the sheath can be potentially pinched between the distal clevis 210 and the proximal clevis 205, particularly as the amount of articulation increases. In some instances, the pinching can result in detrimental wear and tear of the sheath.

Figure 22A:
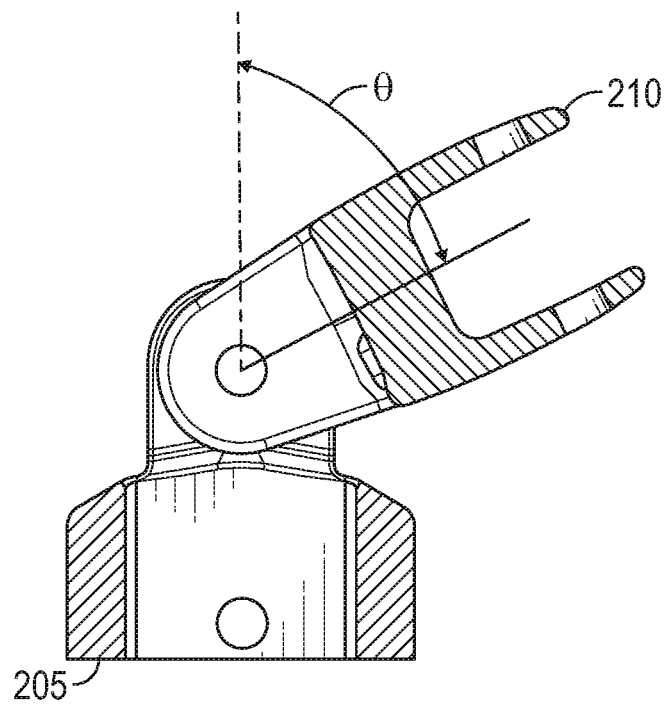
FIGS. 22A and 22B illustrate an embodiment in which the sheath may be pinched in accordance with aspects of this disclosure.
Figure 22B:
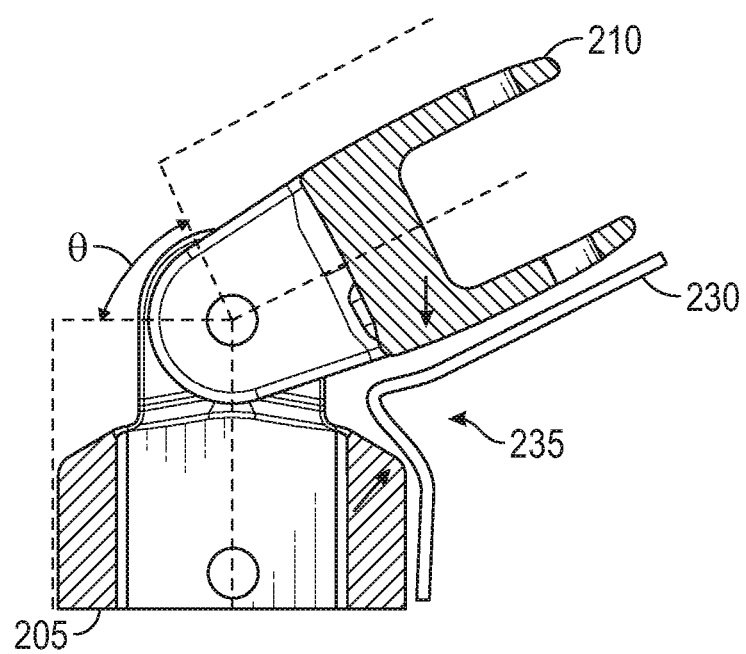

FIGS. 22A and 22B illustrate an embodiment in which the sheath may be pinched in accordance with aspects of this disclosure. Specifically, FIG. 22A illustrates that the distal clevis 210 may be articulated at a varying angle θ with respect to the proximal clevis 205. In FIG. 22B, a portion of the sheath 230 is illustrated as being located at a pinch point 235 between the proximal and distal clevises 205 and 210. With repeated articulation, the sheath 230 may be worn down and/or torn at the pinch point 235, leading to premature wear on the sheath 230 and decreasing the life of the sheath 230. Instrument embodiments described below reduce the risk of wear and/or tear of the sheath.

A. Example Shielded Wrist Having a Frame.

Figure 23A:
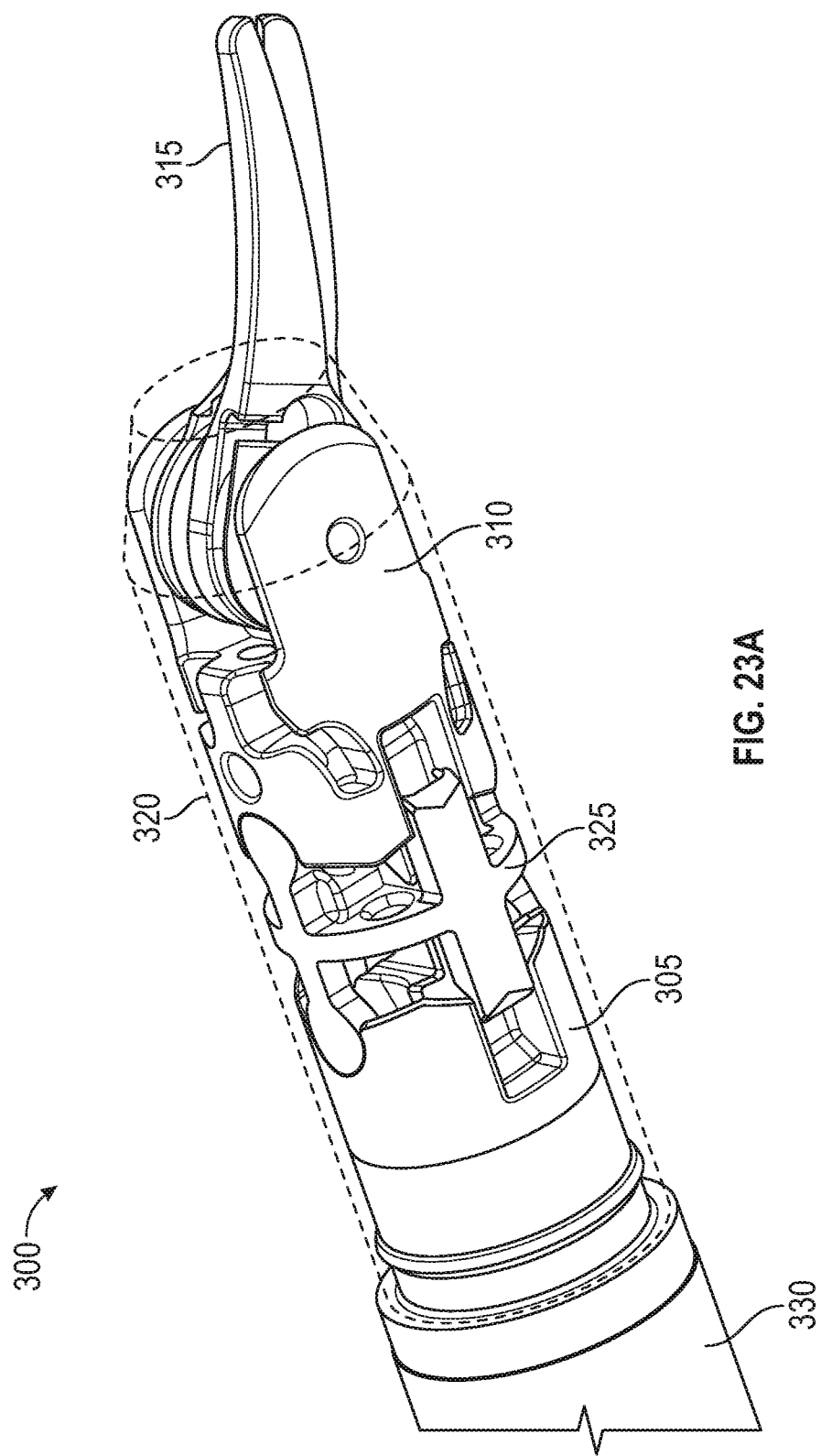
FIGS. 23A-23C provide views of an example instrument including a shielded wrist in accordance with aspects of this disclosure.
Figure 23B:
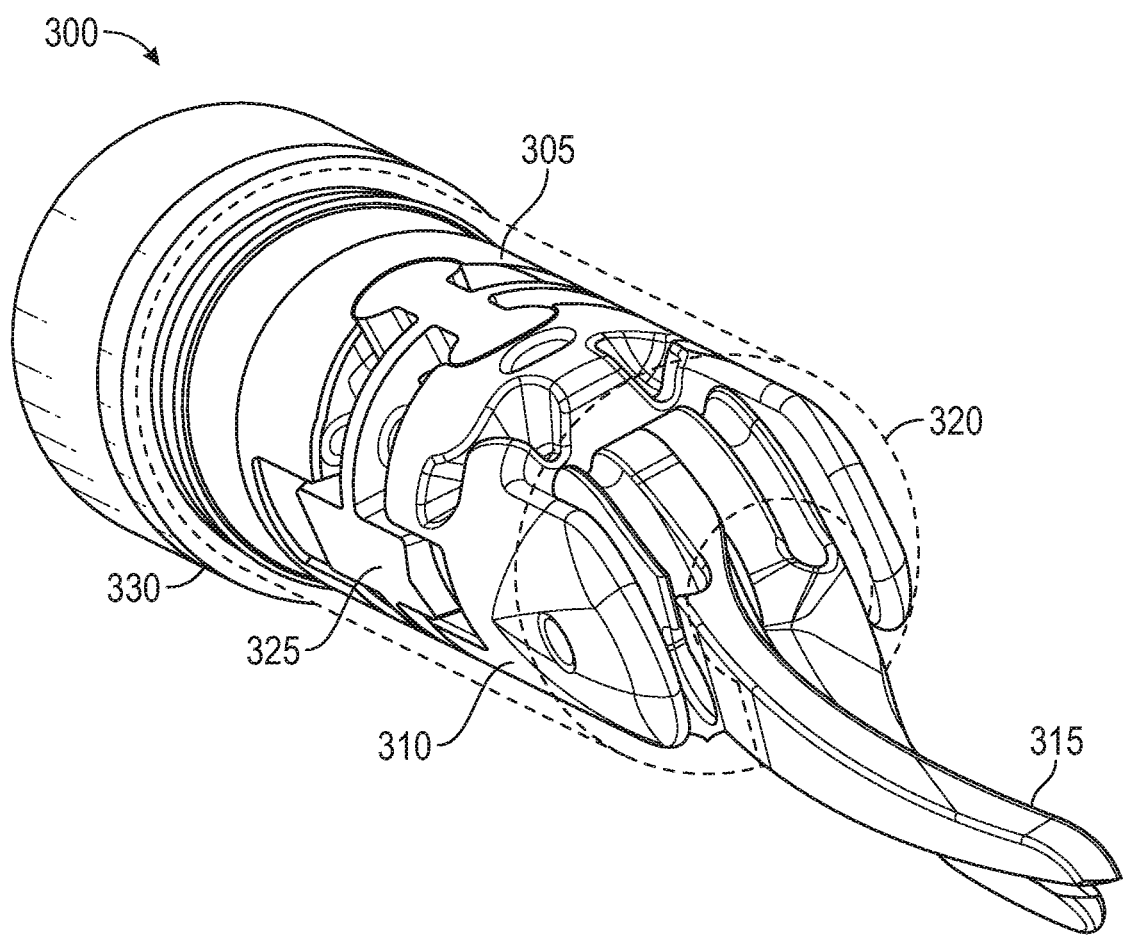
Figure 23C:
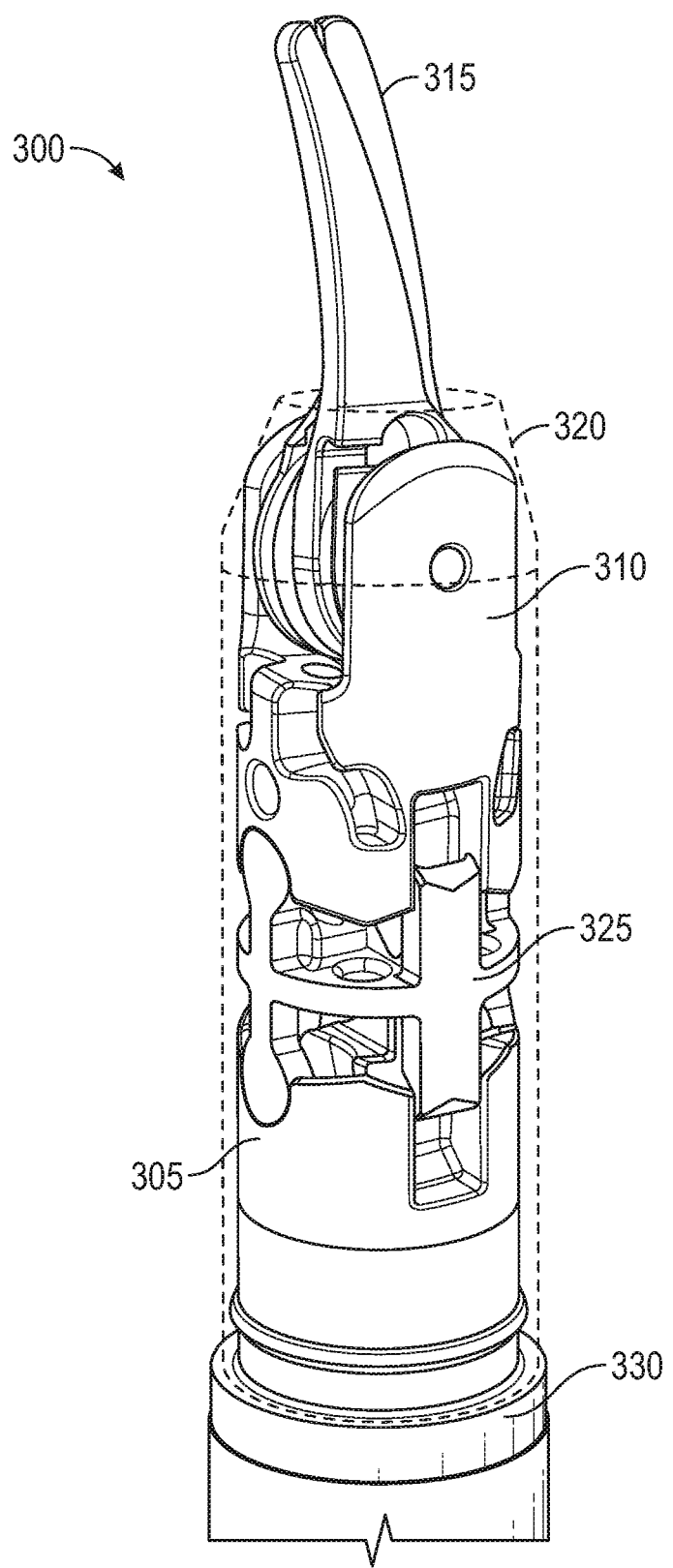

Aspects of this disclosure relate to embodiments of wristed instruments which reduce and/or prevent premature wear due to pinching of the sheath between portions of an articulating wrist. FIGS. 23A-23C provide views of an example instrument including a shielded wrist in accordance with aspects of this disclosure. Referring to FIGS. 23A-23C, the instrument 300 includes a proximal clevis 305, a distal clevis 310, an end effector 315, a sheath 320, a frame 325 (also referred to as a "cage"), and a shaft 330. The sheath 320 can be formed to extend from the shaft to cover a portion of the end effector 315, thereby covering the wrist including the proximal clevis 305, the distal clevis 310, and the frame 325.

Figure 24:
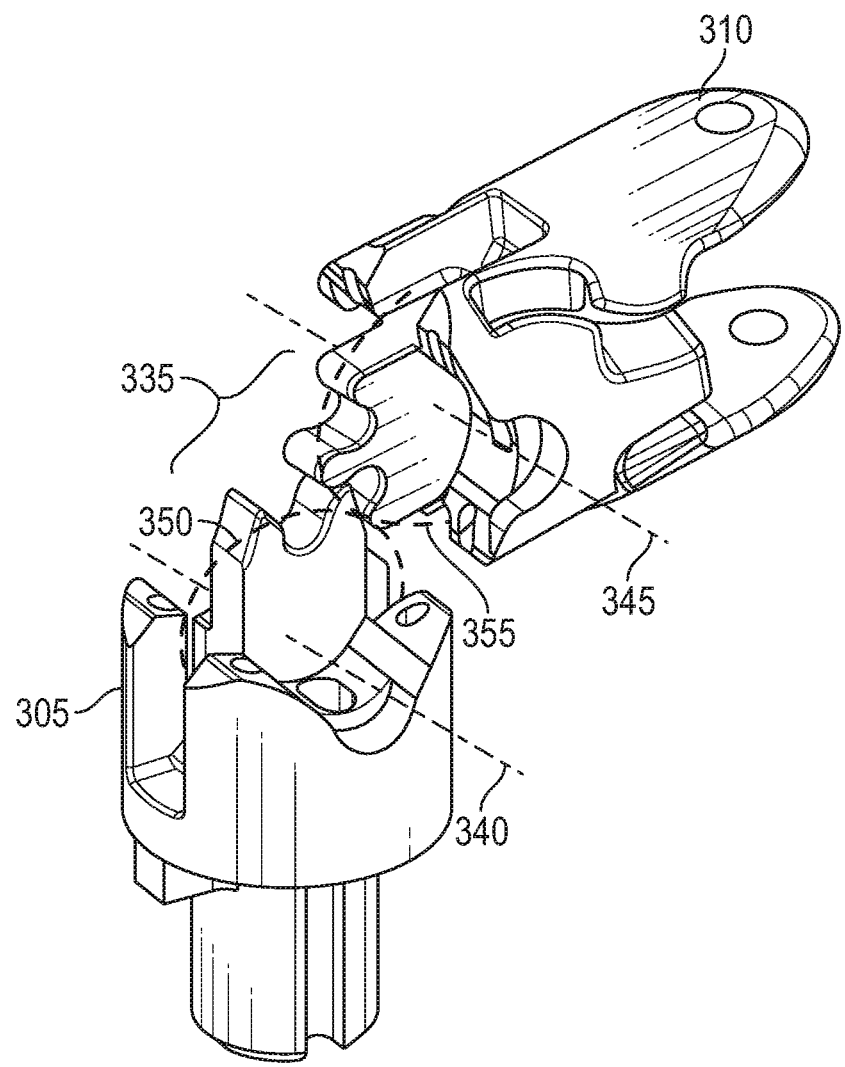
FIG. 24 illustrates an example joint formed between a proximal clevis and a distal clevis in accordance with aspects of this disclosure.

FIG. 24 illustrates an example joint formed between a proximal clevis and a distal clevis in accordance with aspects of this disclosure. Specifically, in FIG. 24, an interface between the proximal clevis 305 and the distal clevis 310 is shown without the other components of the instrument in order to focus on certain aspects of the joint 335. The interface may comprise a rolling joint 335 formed via one or more "teeth" on each of the proximal and distal clevises 305 and 310. As shown in FIG. 24, a tooth or protrusion on the distal clevis 310 engages with an opening or groove formed between teeth on the proximal clevis 305 to form the rolling joint 335. In some embodiments, the rolling joint 335 is embodied in the form of a cycloidal joint.

In contrast to the use of a pin joint, the rolling joint 335 does not have a fixed pivot axis. For example, the rolling joint 335 may define a proximal pitch axis 340 and a distal pitch axis 345. Together, the proximal pitch axis 340 and the distal pitch axis 345 provide two functional pivots for the pitch degree of freedom of the wrist. When embodied as a cycloidal joint, the rolling joint 335 may define pitch circles 350 and 355, respectively centered around the proximal pitch axis 340 and a distal pitch axis 345. The pitch circles 350 and 355 may define certain aspects of the articulation of the wrist including, for example, how the distal pitch axis 345 rotates with respect to the proximal pitch axis 340 during articulation of the wrist.

Figure 25A:
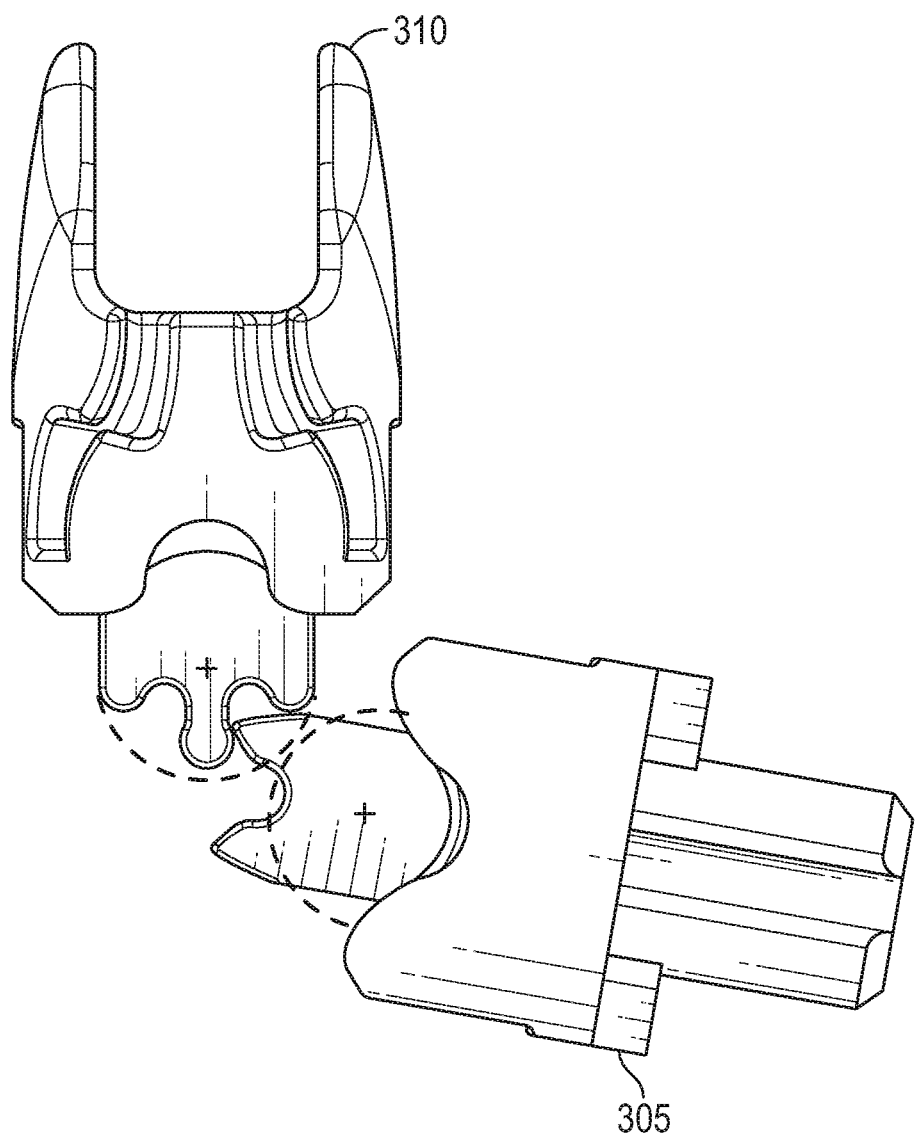
FIGS. 25A-25C illustrate side views of an example wrist in accordance with aspects of this disclosure.
Figure 25B:
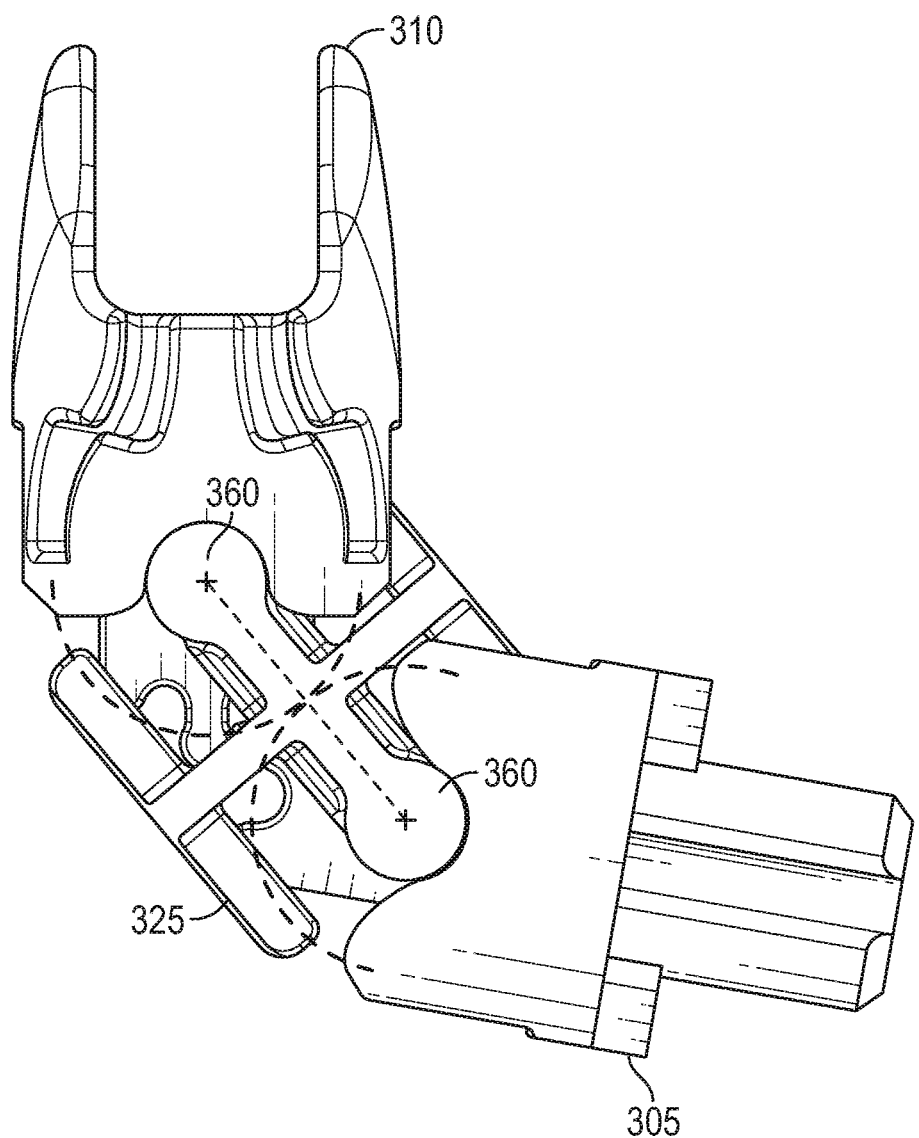
Figure 25C:
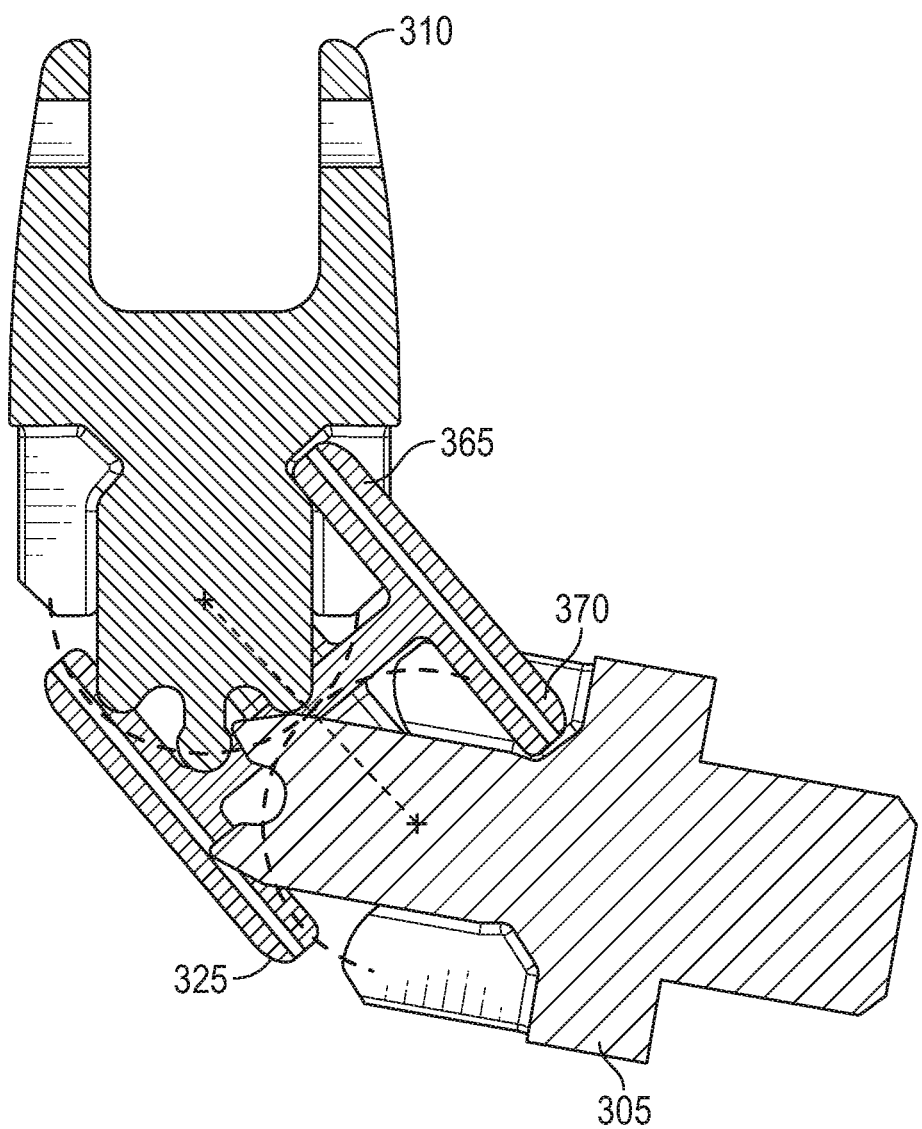

FIGS. 25A-25C illustrate side views of an example wrist in accordance with aspects of this disclosure. Specifically, FIG. 25A illustrates a side view of the wrist without the frame 325, whereas FIG. 25B illustrates a side view of the wrist including the frame 325, and whereas FIG. 25C illustrates a cross-sectional side view of the wrist including the frame 325. As shown in FIGS. 25A-25C, the frame 325 may be positioned between the proximal clevis 305 and the distal clevis 310. The frame 325 includes a plurality of joint posts 360 including ball ends configured to mate with a corresponding socket in each of the proximal clevis 305 and the distal clevis 310. In certain embodiments, the frame 325 may be held in place with respect to the proximal clevis 305 and the distal clevis 310 due to tension in one or more pull wires that extend through the proximal clevis 305 and the frame 325 to the distal clevis 310.

In some embodiments, the frame 325 advantageously functions as a mechanical stop to limit the pitch angle between the proximal clevis 305 and the distal clevis 310 during articulation. In some embodiments, the frame 325 includes a plurality of distally extending posts 365 and a plurality of proximally extending posts 370. In order to provide the limit in the pitch angle, at least some of the distally extending posts 365 may engage corresponding surfaces on the distal clevis 310 at the same time that at least some of the proximally extending posts 370 engage corresponding surfaces on the proximal clevis 305. Thus, the frame 325 can serve as a mechanical stop that limits the pitch angle between the proximal and distal clevis 305 and 310. The frame can advantageously help to (i) constrain the rotation of the rolling joint 335 and (ii) physically block the sheath from being pinched between the two clevises when the wrist is articulated to full pitch.

Figure 26A:
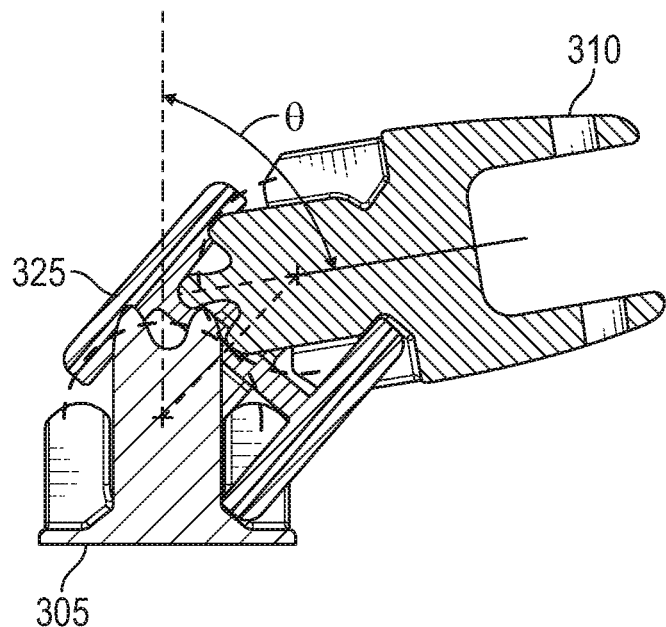
FIGS. 26A and 26B illustrate side views of an example wrist and sheath in accordance with aspects of this disclosure.
Figure 26B:
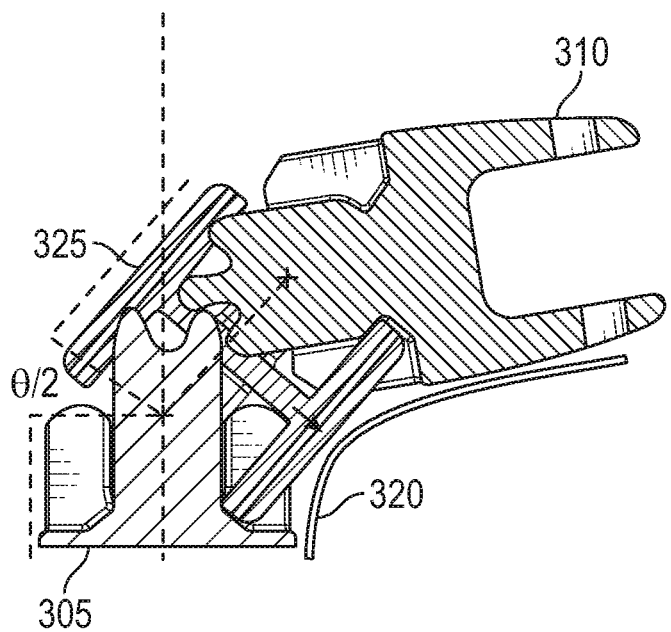

FIGS. 26A and 26B illustrate side views of an example wrist and sheath in accordance with aspects of this disclosure. In particular, FIG. 26A illustrates a side view of the wrist without the sheath 320, whereas FIG. 26B illustrates a side view of the wrist including the sheath 320. With reference to FIG. 26A, the wrist is articulated to the full pitch angle θ at which the frame 325 contacts surfaces of each of the proximal and distal clevises 305 and 310. As can be seen from FIG. 26B, at full pitch, the angle θ/2 formed between the frame 325 and the proximal clevis 305 is half of the full pitch angle θ. Additionally, the frame 325 may block the sheath 320 from being pinched between surfaces of the proximal clevis 305 and the distal clevis 310. For example, the presence of the frame 325 physically moves the sheath 320 away from a region in which the sheath 320 can be potentially pinched (e.g., regions 220 and 225 of FIG. 21).

The use of the rolling joint 335 can reduce the maximum strain on the sheath 320. For example, without the use of the rolling joint 335, if the sheath 230 is approximated as a tubular surface with a radius R, then the maximum travel that the sheath 230 will be stretched at any point along its length is the arc length of Rθ, where θ is the pitch angle of the wrist (e.g., see FIG. 22B). In contrast, using the rolling joint 335, if the sheath 320 has the same radius R, due to the symmetrical nature of the frame 325 in certain embodiments, the arc length is dropped by half to θ/2 for the maximum travel that the sheath 320 will be stretched at any point along its length (e.g., see FIG. 26B).

Figure 27A:
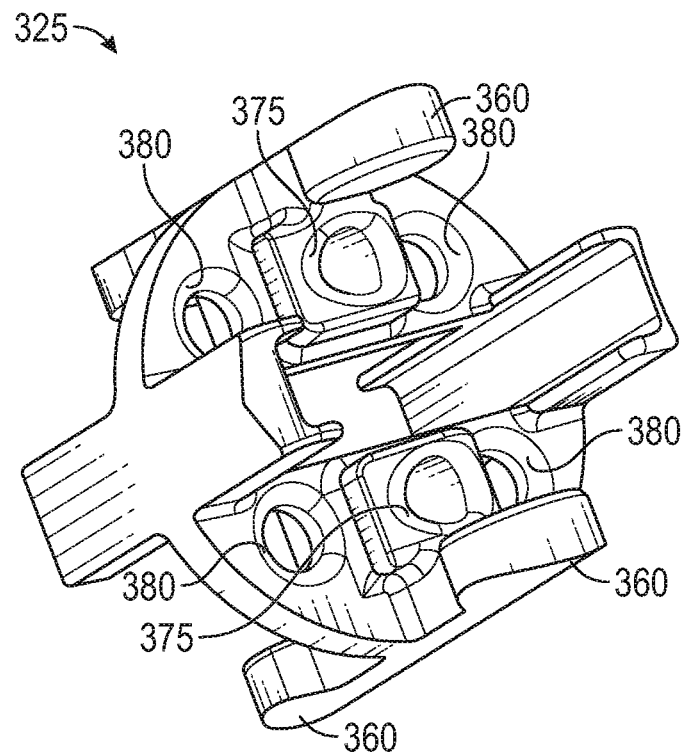
FIGS. 27A and 27B illustrate isometric and side view of an example frame in accordance with aspects of this disclosure.
Figure 27B:
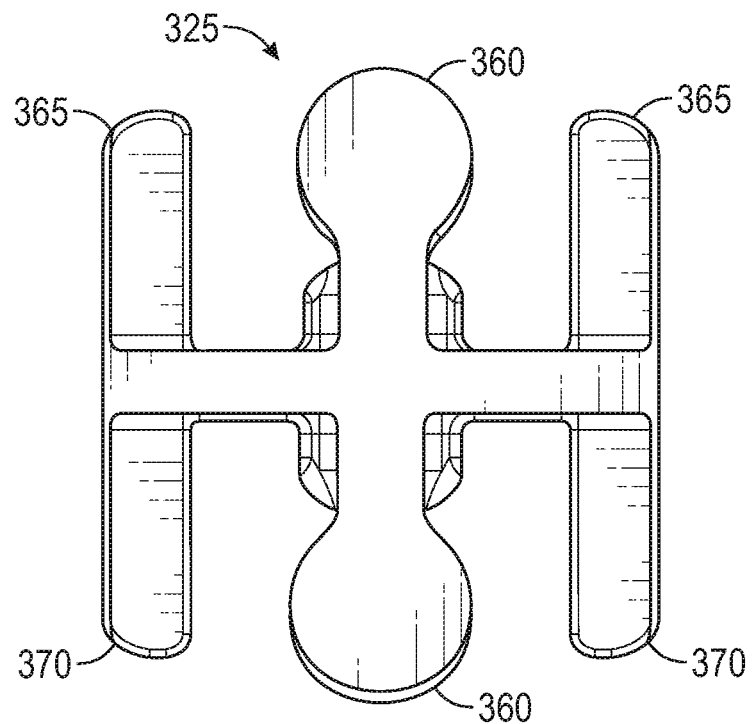

FIGS. 27A and 27B illustrate isometric and side views of an example frame in accordance with aspects of this disclosure. As shown in FIGS. 27A and 27B, the frame 325 includes the joint posts 360, the distally extending posts 365, and the proximally extending posts 370. Advantageously, the frame 325 further includes a plurality of openings or channels 375 and 380 formed to allow wires to pass through the frame 325. The channels 375 may be configured to guide electrical wire(s) through the frame 325 to deliver electrical current to the end effector. In certain embodiments, the electrical wires may be configured to apply current to the end effector. The channels 380 may be configured to guide one or more pull wires through the frame 325 to articulate one or more of the end effector and the wrist (e.g., the distal clevis 310).

Figure 28A:
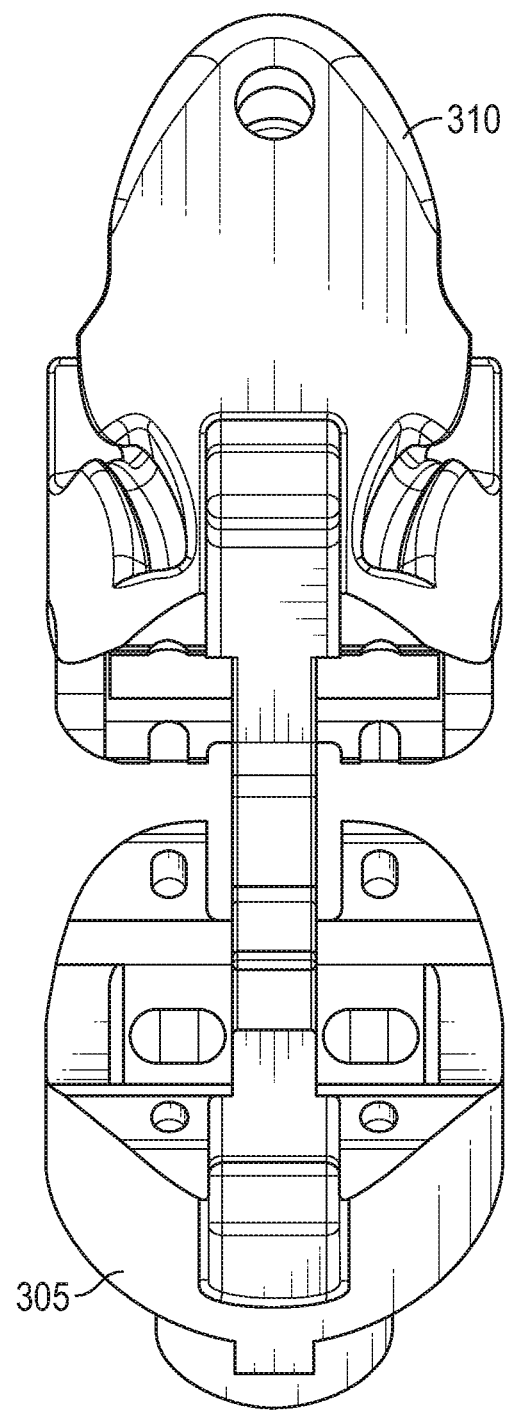
FIGS. 28A-28C illustrate a plurality of views of an example wrist including a frame in accordance with aspects of this disclosure.
Figure 28B:
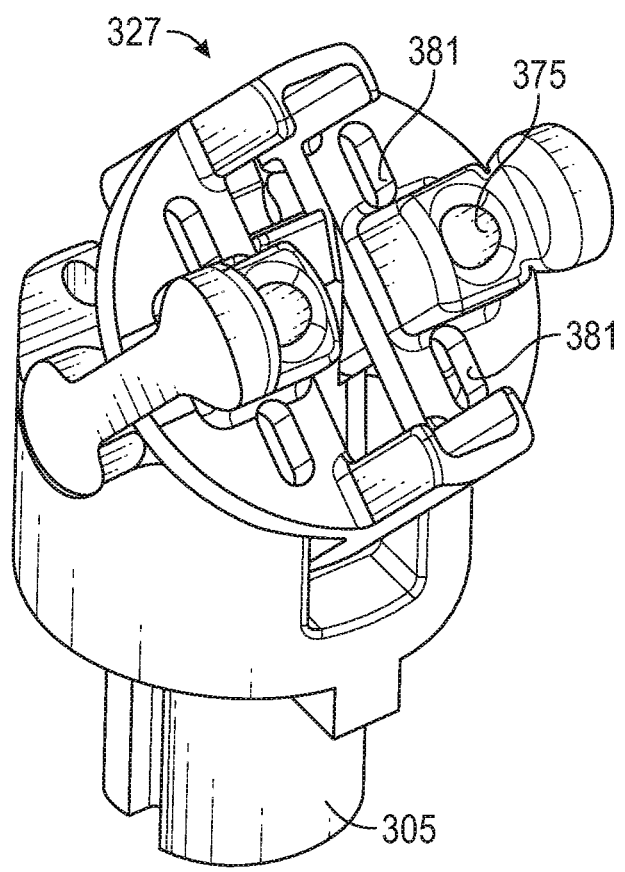
Figure 28C:
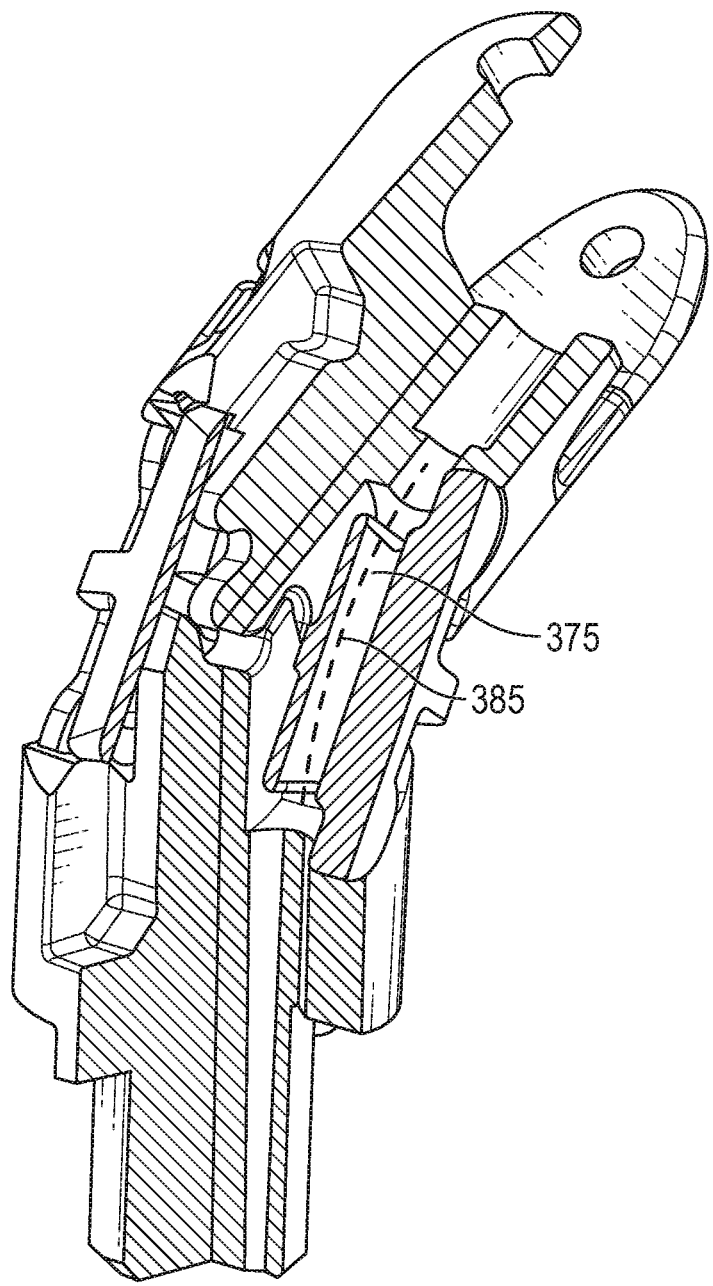

FIGS. 28A-28C illustrate a plurality of views of an example wrist including a frame in accordance with aspects of this disclosure. The frame 327 of FIGS. 28A-28C includes a plurality of channels 375 and 381. In this embodiment, the channels 381 have the shape of a slot rather than the circular shape of the channels 375. Also illustrated is a pathway 385 formed by the channels 375 along which the electrical wire(s) can be guided through the frame 327. The pathways 385 may be configured to shield the electrical wire(s) from the teeth forming the rolling joint between the proximal and distal clevises 305 and 310.

The joint(s) and frame(s) illustrated in the embodiments of FIGS. 23-28 may be configured to reduce the risk of pinch and wear on the sheath. The intermediary frame can serve as a physical stop that works in conjunction with the rolling joint to physically block the sheath from being pinched between proximal and distal clevises 305 and 310 at full pitch. Additionally, in certain embodiments, the wrist architecture advantageously provides a pathway for structures such as electrical wires or tubing such that the wires/tubing can easily be incorporated into the instrument and protected from wear (e.g., from the teeth forming the rolling joint). Thus, the rolling joint provides space that allows electrical wire or tubing to be delivered therethrough.

In order to actuate one of the instruments illustrated in FIGS. 23-28, an instrument driver may advance and/or retract at least one cable segment that engages a distal clevis of the instrument. The wrist, as shown in the figures, can include a proximal clevis, a distal clevis, and an intermediary frame positioned between the proximal clevis and the distal clevis. The advancing or retracting of the at least one cable segment articulates the distal clevis with respect to the proximal clevis. The instrument driver may further rotate the distal clevis with respect to a pitch axis that lies perpendicular to the longitudinal axis of the tool shaft by advancing or retracting at least one cable segment. In certain embodiments, the instrument driver may rotate the distal clevis with respect to the proximal clevis along the rolling joint.

B. Further Example Shielded Wrist Having a Pin Joint.

Aspects of this disclosure relate to embodiments which may reduce and/or prevent premature wear due to pinching of the sheath without the use of a frame. This disclosure may also relate to embodiments of an instrument in which a wire configured to provide a signal from an electrosurgical generator to end effector(s) terminates in a fashion that does not compromise the integrity of the signal during articulation of the instrument wrist. This disclosure may further relate to embodiments of an instrument in which the range of motion for the instrument wrist can be determined mechanically and through software. It is desirable to provide both (i) a software constraint, which can limit mechanical wear and (ii) a mechanical constraint, which can prevent unexpected motions in case of software failure. The mechanical constraint can be enforced through clevis to clevis surface collisions. These collisions can be especially damaging in cases where a sheath is used to cover at least a portion of the wrist, such as the insulating sheath which can be used on, e.g., monopolar shears.

Figure 29:
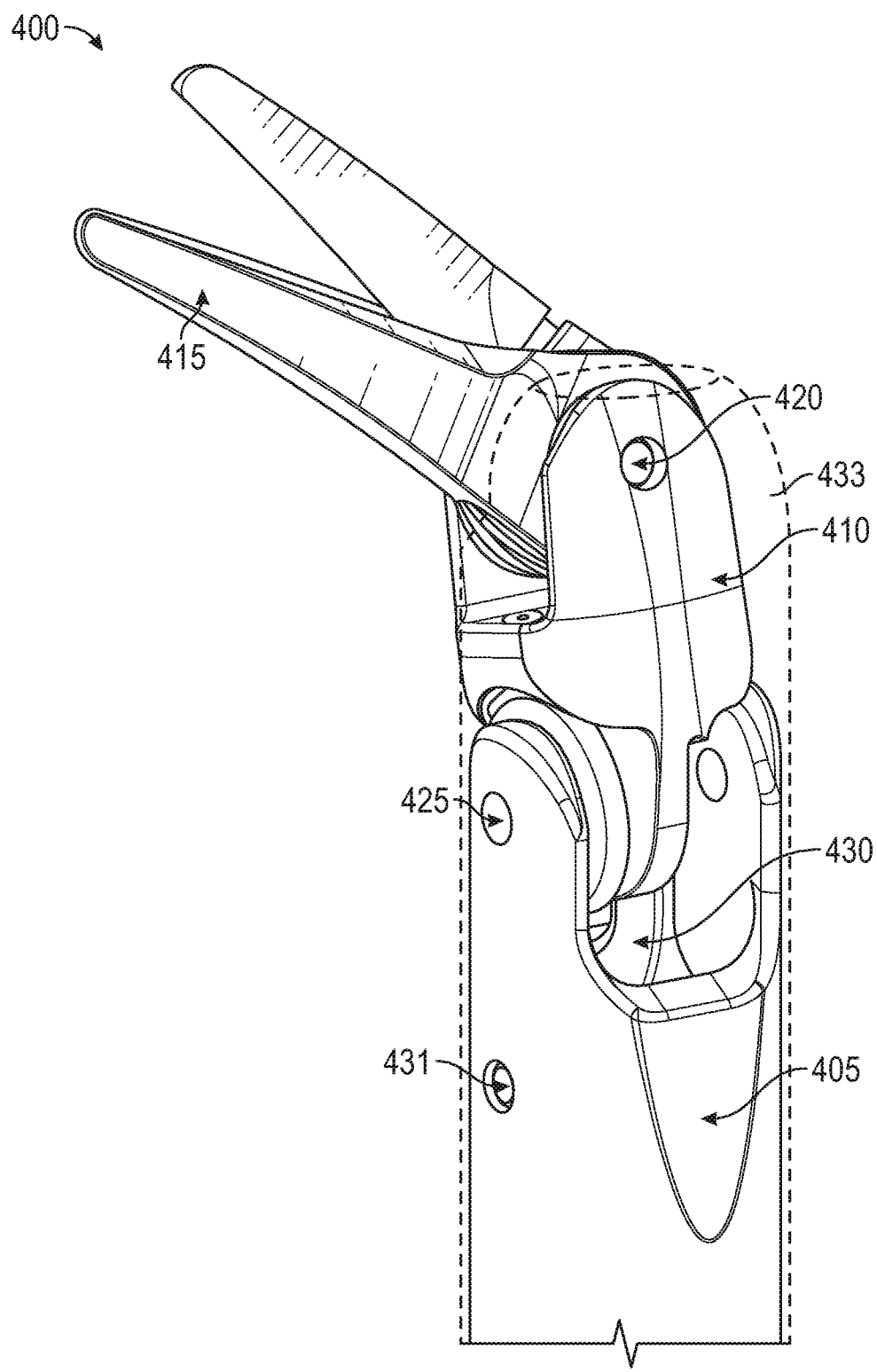
FIG. 29 illustrates an example instrument in accordance with aspects of this disclosure.

FIG. 29 illustrates an example instrument in accordance with aspects of this disclosure. The instrument 400 includes a proximal clevis 405, a distal clevis 410, an end effector 415, a yaw axis 420, a pitch axis 425, an electrode 430, an auxiliary axis 431, and a sheath 433. The sheath 433 can be placed over the instrument 400 to cover the proximal and distal clevises 405 and 410. Advantageously, in some embodiments, the electrode 430 can serve as a hardstop that limits a pitch angle between the proximal clevis 405 and the distal clevis 410, thereby reducing the risk of pinching and tearing of the sheath 433.

Figure 30A:
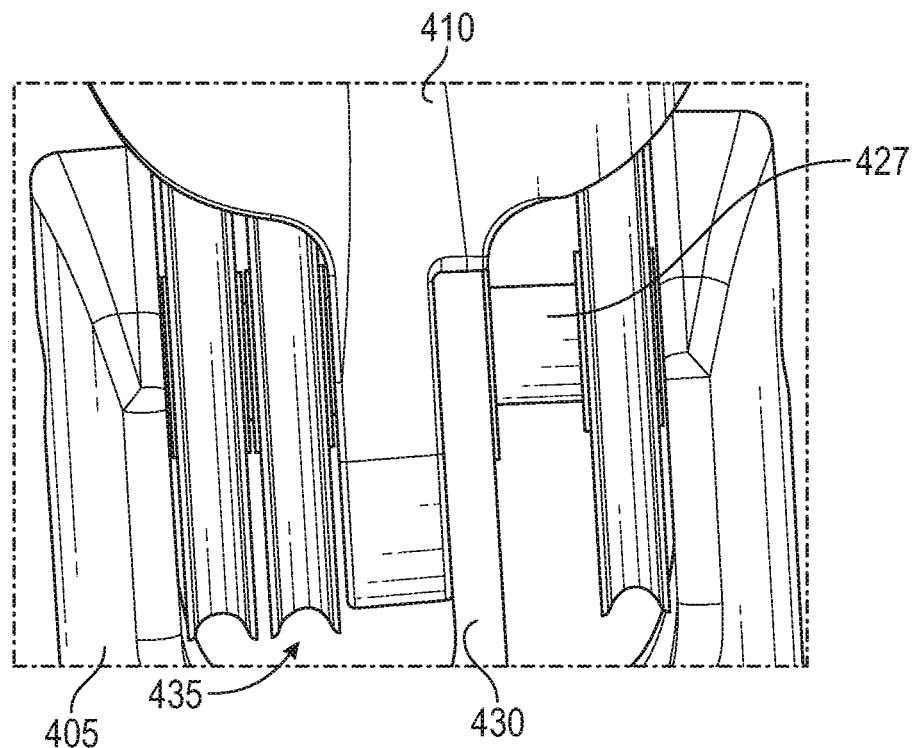
FIGS. 30A-30C provide close up views of the pitch axis illustrated in FIG. 29.
Figure 30B:
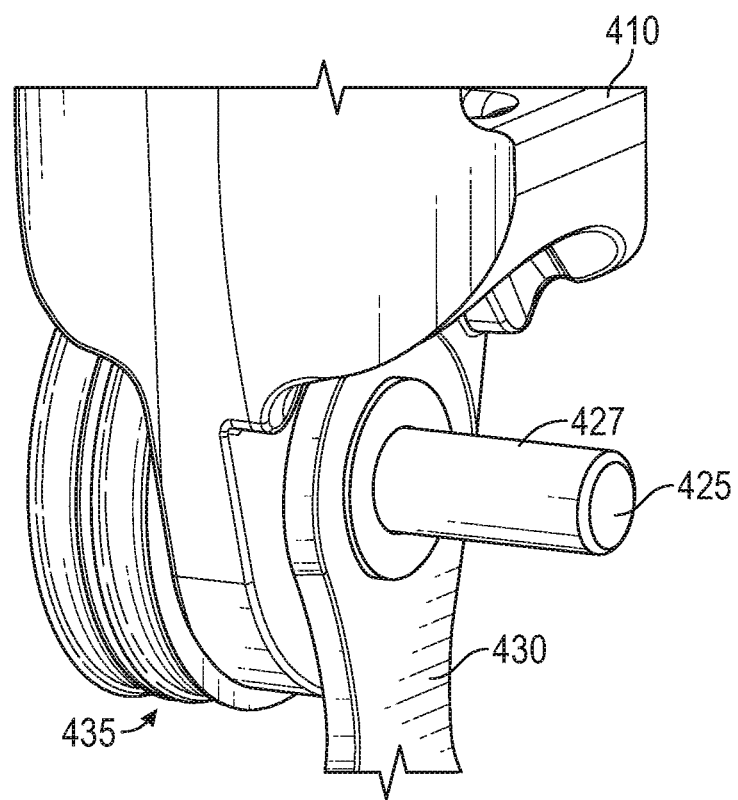
Figure 30C:
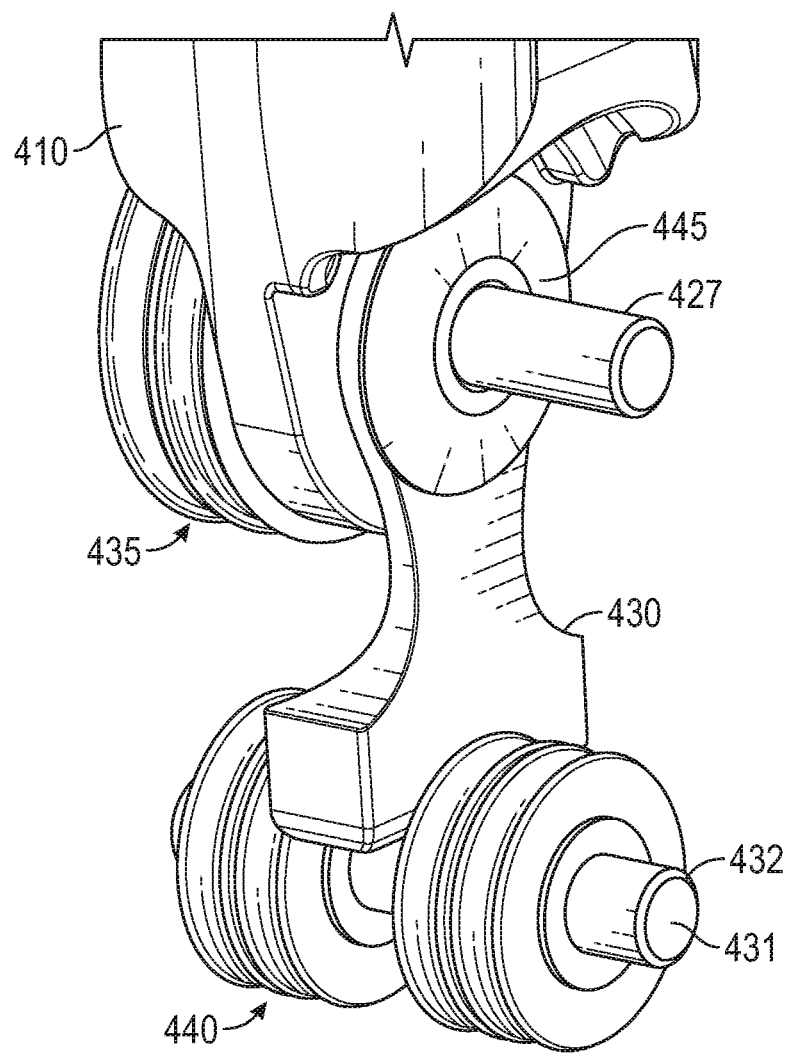

FIGS. 30A-30C provide close up views of the pitch axis illustrated in FIG. 29. The pitch axis 425 may include a pitch pin 427 formed in the proximal clevis 405. Each of the distal clevis 410, the electrode 430, and a plurality of pitch pulleys 435 can be coupled to the pitch pin 427. The pitch pin 427 may form a pin joint connecting the proximal clevis and the distal clevis. Similarly, the auxiliary axis 431 may include an auxiliary pin 432 formed in the proximal clevis 405. A plurality of auxiliary pulleys 440 can be coupled to the auxiliary pin 432. One or more electrical wires (not illustrated) and one or more pull wires (not illustrated) may be engaged with pitch pulleys 435 and/or the auxiliary pulleys 440.

In order to ensure that integrity of the signal provided by the electrode 430 is not affected due to articulation of the wrist, the electrode 430 can function similar to a ring terminal, in which the electrode 430 hangs off the boss on distal clevis 410. A disc spring 445 can also be coupled to the pitch pin 427 in order to maintain contact between the electrode 430 and the distal clevis 410. A larger contact area between the electrode 430 and the wrist can be formed by holding the electrode 430 on the distal clevis 410 using the disc spring 445, thereby reducing the chance that the signal provided to the distal clevis 410 via the electrode 430 is affected by articulation of the wrist. By positioning the electrode 430 on the pitch pin 427 in direct contact with the distal clevis 410, the rotation of the distal clevis 410 against the electrode 430 during articulation helps to abrade/remove potential oxide buildup on the electrode 430 and/or the distal clevis 410. The shape of the electrode 430 can also aid with alignment of the pitch pulleys 435.

Figure 31A:
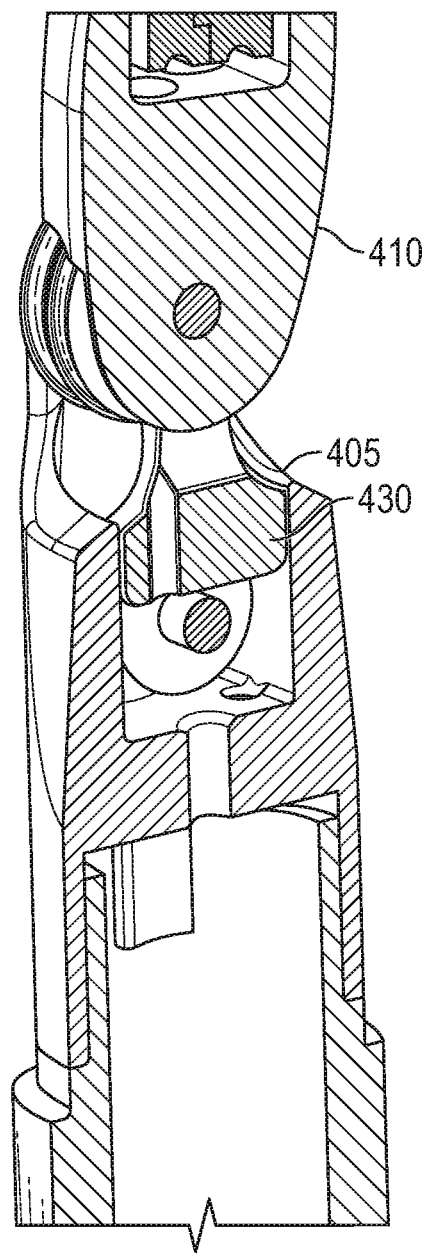
FIGS. 31A and 31B illustrate the hardstop provided as the distal clevis contacts the electrode, rather than the proximal clevis, in accordance with aspects of this disclosure.
Figure 31B:
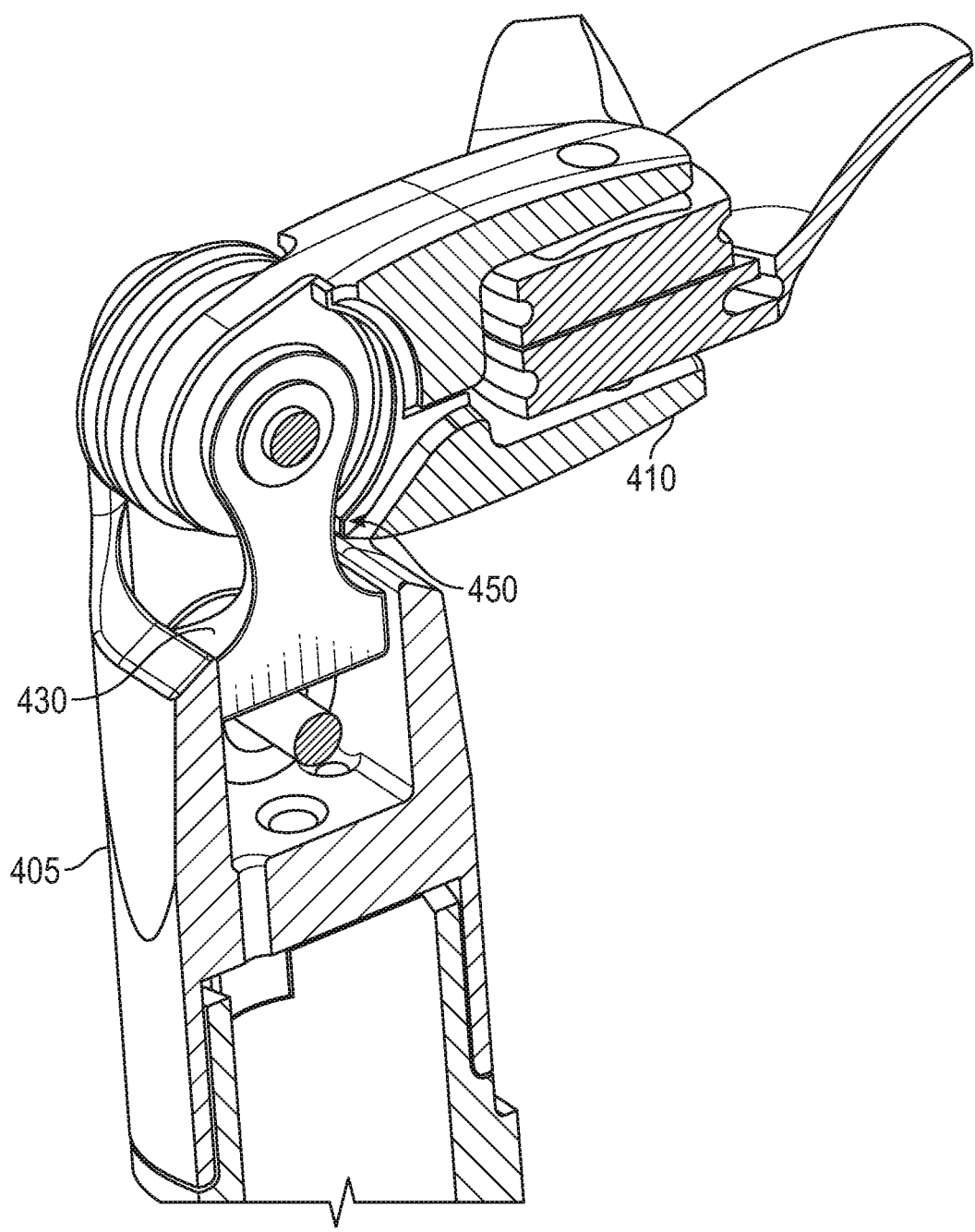

The design of the electrode 430 may simplify the structure of the wrist, reducing the costs associated with machining the instrument 400. Additionally, as noted above, the electrode 430 can be used as a hardstop to prevent surface of the proximal clevis 405 and the distal clevis 410 from pinching and/or perforating the sheath 433. Accordingly, the hardstop can serve as a mechanical stop to limit a pitch angle between the proximal clevis 405 and the distal clevis 410. FIGS. 31A and 31B illustrate the hardstop 450 provided as the distal clevis 410 contacts the electrode 430, rather than the proximal clevis 405, in accordance with aspects of this disclosure.

In limiting the range of motion of the articulation of the distal clevis 410 to provide the hardstop 450, the width of the electrode 430 may determine the possible pitch angle achievable by the distal clevis 410 around the pitch axis before reaching the mechanical hardstop 450. The hardstop 450 prevents the proximal and distal clevises 405 and 410 from pressing down on any portion of the sheath 433. In certain embodiments, due to the shapes of the proximal and distal clevises 405 and 410, the proximal and distal clevises 405 and 410 may have line contact if no hardstop 450 is provided. Thus, the pressure between the proximal and distal clevises 405 and 410 can act as a blade, shearing the sheath 433. By preventing contact between the proximal and distal clevises 405 and 410, breaks or cuts in the sheath 433 can be prevented.

Figure 32:
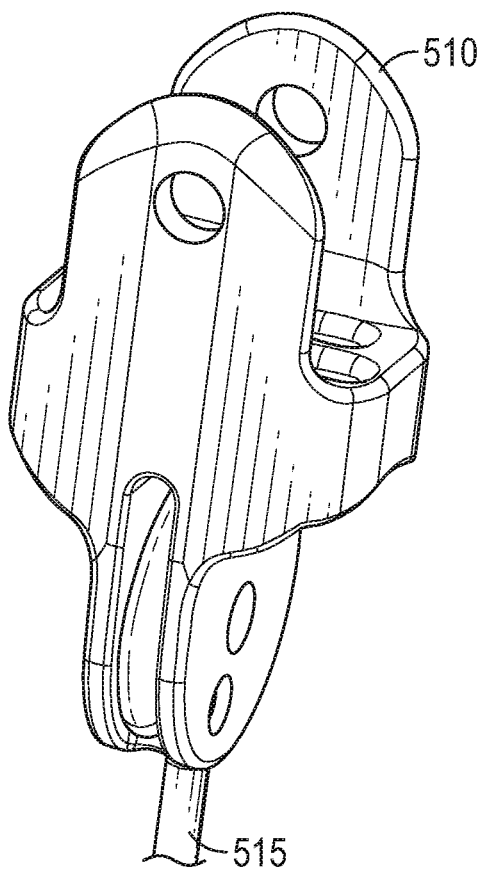
FIG. 32 illustrates another embodiment of the distal clevis in accordance with aspects of this disclosure.

In certain embodiments, the disc spring 445 and electrode 430 can be combined into a single piece. For example, a hooked piece, or spring piece that ends up enclosing the boss on the electrode 430 can be used instead of a ring. FIG. 32 illustrates another embodiment of the distal clevis in accordance with aspects of this disclosure. As shown in FIG. 32, the electrode 515 can be routed through a hole on the distal clevis 510 ear instead of via a boss. In some embodiments, the electrode 515 can be formed of wire 515 instead of sheet metal. In other embodiments, contact pins/plunger electrodes can also be installed within the distal clevis to carry a signal from an electrode sitting in a plastic proximal clevis.

Figure 33:
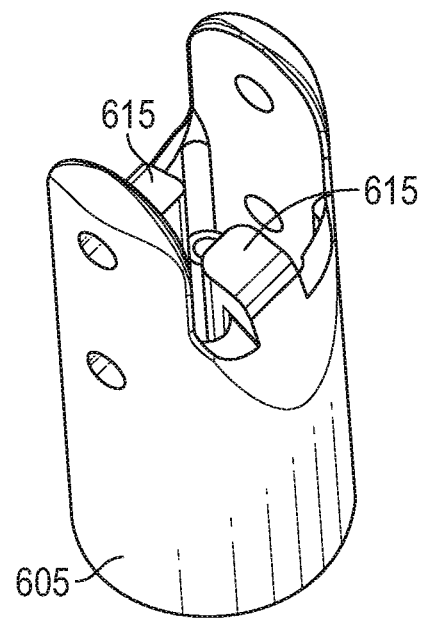
FIG. 33 illustrates another embodiment of the proximal clevis in accordance with aspects of this disclosure.
Figure 34:
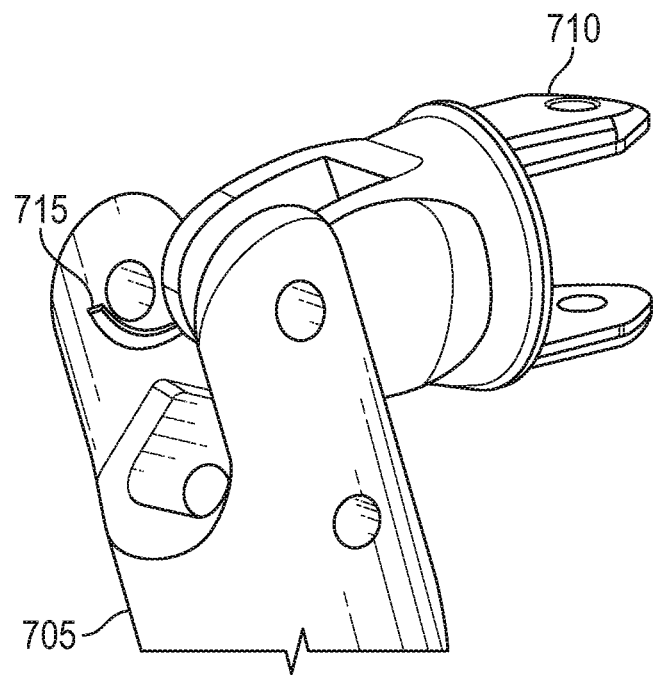
FIG. 34 illustrates yet another embodiment of the proximal and distal clevises in accordance with aspects of this disclosure.

FIG. 33 illustrates another embodiment of the proximal clevis in accordance with aspects of this disclosure. With reference to FIG. 33, instead of a ring terminal, hardstops 615 can be built into the internal spacing of the proximal clevis 605. FIG. 34 illustrates yet another embodiment of the proximal and distal clevises in accordance with aspects of this disclosure. With reference to FIG. 34, a pin (not illustrated) and slot 715 feature can be incorporated into the proximal clevis 705 and distal clevis 710, respectively, to provide the hardstop feature.

3. Implementing Systems and Terminology

Implementations disclosed herein provide systems and apparatuses for shielded wrists, and methods for actuating instruments with wrists.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The shielded wrist functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. An instrument, comprising:
    a shaft;
    an end effector;
    a wrist connecting the shaft to the end effector and including a proximal clevis and a distal clevis, the proximal clevis being in contact with the distal clevis via one or more proximal teeth defined by the proximal clevis and in mated engagement with one or more distal teeth defined by the distal clevis, the proximal clevis and the distal clevis forming a rolling joint as the wrist articulates ; and
    an intermediary frame positioned between the proximal and distal clevises and including:
        first and second joint posts each having opposing ball ends engageable with corresponding sockets defined in the proximal and distal clevises; and
        a plurality of distally and proximally extending stop posts angularly offset from the first and second joint posts by 90° and engageable with the proximal and distal clevises when the wrist articulates.

2. The instrument of claim 1, wherein the intermediary frame defines one or more channels, and the instrument further comprises one or more wires extending through the one or more channels.

3. The instrument of claim 2, wherein the one or more wires comprise electrical wires to deliver electrical current to the end effector.

4. The instrument of claim 2, wherein the one or more wires comprise pull wires configured to articulate one or more of the end effector and the wrist.

5. The instrument of claim 1, further comprising a sheath that extends over the wrist.

6. The instrument of claim 5, wherein the plurality of distally and proximally extending stop posts to block the sheath from being pinched between surfaces of the proximal clevis and the distal clevis.

7. An instrument, comprising:
    a shaft;
    a wrist operatively coupled to the shaft and including a proximal clevis and a distal clevis, the proximal clevis defining one or more proximal teeth and the distal clevis defining one or more distal teeth in mated engagement with the one or more proximal teeth to form a rolling joint as the wrist articulates; and
    an intermediary frame positioned between the proximal and distal clevises and including a central body that defines a central aperture and provides first and second joint posts extending from the central body, each joint post having opposing ball ends engageable with corresponding sockets defined in the proximal and distal clevises,
    wherein the one or more proximal teeth and the one or more distal teeth extend through the central aperture, and
    wherein the rolling joint defines parallel proximal and distal pitch axes.

8. The instrument of claim 7, wherein the intermediary frame comprises one or more distally extending posts configured to contact a surface of the distal clevis and one or more proximally extending posts configured to contact a surface of the proximal clevis to provide the limit to a pitch angle between the proximal and distal clevises.

9. The instrument of claim 7, wherein the instrument further comprises a sheath that extends over the proximal clevis and the distal clevis.

10. The instrument of claim 9, wherein the sheath is formed of an elastomeric material.

11. An instrument, comprising:
    a shaft;
    an end effector;
    a wrist connecting the shaft to the end effector and including a proximal clevis and a distal clevis that are in contact with each other during rotational movement of the wrist, the proximal clevis defining one or more proximal teeth and the distal clevis defining one or more distal teeth in mated engagement with the one or more proximal teeth to form a rolling joint as the wrist articulates, wherein the proximal clevis defines a proximal pitch axis and the distal clevis defines a distal pitch axis parallel to the proximal pitch axis; and
    an intermediary frame interposed between the proximal clevis and the distal clevis and including a central body that provides a plurality of distally and proximally extending stop posts extending from the central body and engageable with, the proximal clevis and the distal clevis upon overrotation during the rotational movement of the wrist and thereby serve as a mechanical stop to limit a pitch angle between the proximal clevis and the distal clevis;
    a sheath that extends over the proximal clevis and the distal clevis, wherein the plurality of distally and proximally extending stop posts block the sheath from being pinched between surfaces of the proximal clevis and the distal clevis as the wrist articulates.

12. The instrument of claim 11, wherein the wrist comprises a pin joint connecting the proximal clevis and the distal clevis.

13. The instrument of claim 11, wherein the intermediary frame further includes first and second joint posts extending from the central body, each joint post having opposing ball ends engageable with corresponding sockets defined in the proximal and distal clevises.

14. The instrument of claim 7, wherein the intermediary frame further includes a plurality of distally and proximally extending stop posts extending from the central body and engageable with the proximal and distal clevises for limiting a pinch angle between the proximal clevis and the distal clevis.

15. The instrument of claim 7, wherein the intermediary frame comprises:
    two proximal stop posts extending in a first direction away from the central body along a longitudinal axis of the intermediary frame, the proximal stop posts being interposed between the first and second joint posts about a circumference of the intermediary frame; and
    two distal stop posts extending in a second direction, opposite the first direction, away from the central body along the longitudinal axis, the distal stop posts being interposed between the first and second joint posts about the circumference of the intermediary frame,
    wherein the proximal stop posts and the distal stop posts are rotationally aligned with each other.

16. The instrument of claim 1, wherein the proximal joint post comprises a proximal ball end configured to mate with the socket in the proximal clevis.

17. The instrument of claim 16, wherein the distal joint post comprises a distal ball end configured to mate with the socket in the distal clevis.

18. The instrument of claim 1, wherein the distally extending stop posts are engageable with the distal clevis and the proximally extending stop posts are engageable with the proximal clevis to limit a pitch angle between the proximal and distal clevises.

19. The instrument of claim 1, wherein sliding engagement between the opposing ball ends and the corresponding sockets defines a proximal pitch axis and a distal pitch axis of the wrist, and wherein the proximal pitch axis is parallel to the distal pitch axis.

20. The instrument of claim 13, wherein the plurality of distally and proximally extending stop posts are angularly offset from the first and second joint posts about the central body by 90°.

21. The instrument of claim 14, wherein the plurality of distally and proximally extending stop posts are angularly offset from the first and second joint posts about the central body by 90°.

\* \* \* \* \*